(12) United States Patent
Frye et al.

(10) Patent No.: US 10,730,524 B2
(45) Date of Patent: Aug. 4, 2020

(54) VEHICLE SEAT

(71) Applicant: Faurecia Automotive Seating, LLC, Auburn Hills, MI (US)

(72) Inventors: Dale J. Frye, West Olive, MI (US); James T. Hotary, Holland, MI (US); Cedric Ketels, Holland, MI (US); Rudy K. Yukich, Columbia, MD (US); Houstin L. Lichtenwalner, Macungie, PA (US); H. Keith Nishihara, Los Altos, CA (US)

(73) Assignee: Faurecia Automotive Seating, LLC, Auburn Hills, MI (US)

( * ) Notice: Subject to any disclaimer, the term of this patent is extended or adjusted under 35 U.S.C. 154(b) by 62 days.

(21) Appl. No.: 15/692,396

(22) Filed: Aug. 31, 2017

(65) Prior Publication Data
US 2018/0065642 A1 Mar. 8, 2018

Related U.S. Application Data

(60) Provisional application No. 62/384,357, filed on Sep. 7, 2016.

(51) Int. Cl.
B60W 40/08 (2012.01)
B60N 2/00 (2006.01)
(Continued)

(52) U.S. Cl.
CPC ........... B60W 40/08 (2013.01); A61B 5/6893 (2013.01); B60N 2/002 (2013.01); B60N 2/0248 (2013.01); B60R 16/037 (2013.01); B60R 21/01512 (2014.10); A61B 5/0077 (2013.01); A61B 5/02055 (2013.01); A61B 5/0816 (2013.01);
(Continued)

(58) Field of Classification Search
CPC ...... B60W 40/09; B60W 40/02; B60W 50/14; B60W 50/0098; B60W 2040/0872; B60W 40/08; B60W 2540/22; B60W 30/146; B60W 50/0097; B60R 21/01512; B60R 25/25; B60R 16/037; B60R 21/0134; B60R 21/015
See application file for complete search history.

(56) References Cited

U.S. PATENT DOCUMENTS 3,580,245 A 5/1971 Dill
4,031,579 A 6/1977 Larned
(Continued)

FOREIGN PATENT DOCUMENTS

CN 1572575 2/2005
CN 1956680 A 5/2007
(Continued)

OTHER PUBLICATIONS

Chinese Rejection Decision for Chinese App. No. 201380064313.2 dated May 17, 2018, 13 pages.
(Continued)

Primary Examiner — Hunter B Lonsberry
Assistant Examiner — Luis A Martinez Borrero
(74) Attorney, Agent, or Firm — Barnes & Thornburg LLP

(57) ABSTRACT

An occupant support adapted for use in a vehicle includes a sensory system and a control system. The sensor system is configured to generate signals indicative of at least one of a physiological characteristic of the occupant.

19 Claims, 16 Drawing Sheets

(51) Int. Cl.
  *B60R 21/015* (2006.01)
  *A61B 5/00* (2006.01)
  *B60N 2/02* (2006.01)
  *B60R 16/037* (2006.01)
  *A61B 5/0205* (2006.01)
  *A61B 5/11* (2006.01)
  *A61B 5/145* (2006.01)
  *A61B 5/08* (2006.01)

(52) U.S. Cl.
  CPC .............. *A61B 5/11* (2013.01); *A61B 5/1103* (2013.01); *A61B 5/14517* (2013.01); *A61B 5/441* (2013.01); *B60W 2040/0818* (2013.01); *B60W 2040/0872* (2013.01); *B60W 2540/043* (2020.02); *B60W 2540/215* (2020.02); *B60W 2540/22* (2013.01)

(56) References Cited

U.S. PATENT DOCUMENTS

| | | | |
|---|---|---|---|
| 4,655,505 A | 4/1987 | Kashiwamura | |
| 4,707,027 A | 11/1987 | Horvath | |
| 4,840,425 A | 6/1989 | Noble | |
| 4,926,090 A | 5/1990 | Yoshimi | |
| 5,069,214 A | 12/1991 | Samaras | |
| 5,155,685 A | 10/1992 | Kishi | |
| 5,462,515 A | 10/1995 | Tseng | |
| 6,055,473 A | 4/2000 | Zwolinski | |
| 6,212,719 B1 | 4/2001 | Thomas | |
| 6,273,810 B1 | 8/2001 | Rhodes, Jr. | |
| 6,422,087 B1 | 7/2002 | Potter | |
| 7,206,631 B2* | 4/2007 | Kawachi | A61B 5/417 600/519 |
| 7,239,945 B2* | 7/2007 | Hiemer | B60W 40/02 701/32.2 |
| 7,322,652 B1 | 1/2008 | Tache | |
| 7,774,052 B2 | 8/2010 | Burton | |
| 7,862,113 B2 | 1/2011 | Knoll | |
| 8,123,290 B1 | 2/2012 | Aiken | |
| 8,181,292 B1 | 5/2012 | Pellettiere | |
| 8,328,279 B2 | 12/2012 | Brncick | |
| 8,430,817 B1 | 4/2013 | Al-Ali | |
| 8,616,654 B2* | 12/2013 | Zenk | B60N 2/914 297/452.41 |
| 8,672,411 B2 | 3/2014 | Gomes | |
| 8,725,311 B1 | 5/2014 | Breed | |
| 8,757,726 B2 | 6/2014 | Oota | |
| 8,919,874 B2 | 12/2014 | Ota | |
| 9,135,803 B1* | 9/2015 | Fields | G06Q 40/08 |
| 9,440,657 B1* | 9/2016 | Fields | G08B 21/06 |
| 9,475,389 B1* | 10/2016 | Fung | B60K 35/00 |
| 9,505,402 B2* | 11/2016 | Fung | B60W 10/22 |
| 9,717,345 B1 | 8/2017 | Caruso | |
| 9,848,814 B2* | 12/2017 | Benson | A61M 21/02 |
| 10,235,859 B1* | 3/2019 | Hiles | B60W 40/09 |
| 10,258,535 B2 | 4/2019 | Lem | |
| 10,471,864 B1 | 11/2019 | Tait | |
| 2002/0091473 A1 | 7/2002 | Gardner | |
| 2004/0243368 A1 | 12/2004 | Hiemer | |
| 2005/0027416 A1 | 2/2005 | Basir | |
| 2005/0124864 A1* | 6/2005 | Mack | A61B 5/024 600/300 |
| 2005/0248184 A1 | 11/2005 | Piffaretti | |
| 2006/0025698 A1 | 2/2006 | Nakagawa | |
| 2006/0068693 A1 | 3/2006 | Kono | |
| 2006/0175877 A1 | 8/2006 | Alionte | |
| 2007/0029862 A1 | 2/2007 | Bargheer | |
| 2007/0251749 A1 | 11/2007 | Breed | |
| 2008/0296946 A1 | 12/2008 | Reynolds | |
| 2009/0030576 A1 | 1/2009 | Periot | |
| 2009/0164241 A1* | 6/2009 | Racioppo | G06Q 10/06 705/2 |
| 2010/0185068 A1 | 7/2010 | Park | |
| 2010/0229181 A1* | 9/2010 | Ahuja | G06F 9/4856 718/107 |
| 2011/0015468 A1* | 1/2011 | Aarts | A61B 5/0205 600/26 |
| 2011/0066292 A1 | 3/2011 | Moriya | |
| 2011/0133755 A1 | 6/2011 | Griffin | |
| 2011/0156453 A1 | 6/2011 | Matsushima | |
| 2011/0186560 A1 | 8/2011 | Kennedy | |
| 2011/0304465 A1 | 12/2011 | Boult | |
| 2012/0078123 A1* | 3/2012 | Futatsuyama | A61B 5/02125 600/485 |
| 2012/0212353 A1 | 8/2012 | Fung | |
| 2013/0070043 A1* | 3/2013 | Geva | B60K 28/066 348/14.02 |
| 2014/0031703 A1* | 1/2014 | Rayner | A61B 5/02055 600/484 |
| 2014/0039330 A1* | 2/2014 | Seo | A61B 5/0452 600/509 |
| 2014/0228649 A1* | 8/2014 | Rayner | A61B 5/1118 600/301 |
| 2014/0240132 A1* | 8/2014 | Bychkov | A61B 5/18 340/576 |
| 2014/0276112 A1* | 9/2014 | Fung | A61B 5/024 600/479 |
| 2015/0008710 A1 | 1/2015 | Young | |
| 2015/0051526 A1 | 2/2015 | Wang | |
| 2015/0151658 A1 | 6/2015 | Burris | |
| 2015/0231991 A1 | 8/2015 | Yetukuri | |
| 2015/0239321 A1 | 8/2015 | Mëller et al. | |
| 2015/0313475 A1* | 11/2015 | Benson | A61B 5/6893 297/217.3 |
| 2016/0001781 A1* | 1/2016 | Fung | G16H 50/20 701/36 |
| 2016/0019813 A1* | 1/2016 | Mullen | G09B 19/00 434/236 |
| 2016/0029940 A1 | 2/2016 | Iizuka | |
| 2016/0086500 A1* | 3/2016 | Kaleal | G06T 19/00 434/257 |
| 2016/0339801 A1 | 11/2016 | Pereny | |
| 2016/0339802 A1 | 11/2016 | Hanlon | |
| 2017/0136842 A1* | 5/2017 | Anderson | B60G 17/016 |
| 2017/0136922 A1 | 5/2017 | Von Ballmoos | |
| 2017/0158202 A1 | 6/2017 | Yang | |
| 2017/0282930 A1* | 10/2017 | Kochhar | B60W 40/09 |
| 2017/0285641 A1* | 10/2017 | Goldman-Shenhar | B60K 28/02 |
| 2017/0312534 A1 | 11/2017 | Cao | |
| 2017/0326013 A1* | 11/2017 | Hyde | A61B 5/6805 |
| 2017/0340214 A1 | 11/2017 | Benson | |
| 2018/0037236 A1* | 2/2018 | Yamaguchi | A61M 21/00 |
| 2018/0178808 A1* | 6/2018 | Zhao | B60N 2/002 |
| 2018/0229674 A1* | 8/2018 | Heinrich | B60R 16/0231 |

FOREIGN PATENT DOCUMENTS

| | | |
|---|---|---|
| CN | 103565429 A | 2/2014 |
| CN | 104837403 A | 8/2015 |
| CN | 0104875744 | 9/2015 |
| DE | 102005038289 | 3/2007 |
| DE | 102007053119 | 5/2009 |
| DE | 102009021532 | 11/2010 |
| EP | 1447070 A | 8/2004 |
| JP | 2010264092 | 11/2010 |
| KR | 1020010061858 | 7/2001 |
| KR | 1020140027641 | 3/2014 |
| KR | 0101642697 | 8/2016 |
| WO | 2013109154 | 7/2013 |
| WO | 2013109154 A1 | 7/2013 |
| WO | 2014147828 | 9/2014 |
| WO | 02014147828 | 9/2014 |
| WO | 2015127193 | 8/2015 |
| WO | 2015200224 | 12/2015 |
| WO | 2016070981 | 5/2016 |

OTHER PUBLICATIONS

Chinese Office Action for Chinese App. No. 201380064313.2 dated Sep. 28, 2017, 19 pages.

(56) References Cited

OTHER PUBLICATIONS

Chinese Office Action for Chinese Pat. App. No. 201580011844.9 dated Aug. 28, 2018, 19 pages, (brief summary included in English).
European Examination Report for European App. No. 15 707 235.6 dated Feb. 18, 7 pages.
Office Action dated Nov. 29, 2017 for U.S. Appl. No. 15/235,882; (pp. 1-7).
Chinese Office Action for Chinese App. No. 201380064313.2 dated Apr. 12, 2017, 21 pages.
PCT International Search Report and Written Opinion completed by the ISA/US on Apr. 22, 2014 and issued in connection with PCT/US2013/071620.
PCT Search Report and Written Opinion completed by the ISA/EP on May 21, 2015 and issued in connection with PCT/US2015/016803, 13 pages.
Chinese Office Action for Chinese Pat. App. No. 201580011844.9 dated Jul. 12, 2019, 13 pages, (brief summary included in English).
Office Action dated May 16, 2019 for U.S. Appl. No. 15/626,525, (pp. 1-12).
Chinese Office Action for Chinese Pat. App. No. 201580011844.9 dated Mar. 14, 2019, 12 pages, (brief summary included in English).
Chinese Office Action for Chinese Pat. App. No. 201580011844.9 dated Nov. 19, 2019, 13 pages, (brief summary included in English).
Chinese Office Action for Chinese App. No. 201710799929.9 dated Sep. 27, 2019, 14 pages.
Fifth Chinese Office Action for Chinese Pat. App. No. 201580011844.9 dated Mar. 13, 2020, 3619 CN II, 13 pages, (brief summary included in English).
Choi et al., "Noninvaisive cuffless blood pressure estimation usingpulse transit time and Hilbert-Huang transform," Computers and Electridal Engineering Journal, 39, 103-111 (Nov. 8, 2012), 9 pages.
Wong et al., "The Effects of Exercises on teh Relationship between Pulse Transit Time and Arterial Blood Pressure," Proceedings of the 2005 IEEE Enginering in Medicine and Biology 27th Annual Conference, Shanghai, China , Sep. 1-4, 2005, 3 pages.
Office Action dated Apr. 27, 2020 for U.S. Appl. No. 15/626,525, 4081 US-U II (pp. 1-11).
Office Action dated Apr. 30, 2020 for U.S. Appl. No. 15/873,034, 4296 US-U II (pp. 1-24).
European Examination Report for European App. No. 15 707 235.6 dated Apr. 15, 2020, 3619 EP II , 5 pages.
Office Action dated Apr. 30, 2020 for U.S. Appl. No. 15/863,129, 4296 US-U II (pp. 1-23).
Office Action dated May 8, 2020 for U.S. Appl. No. 15/613,578, 4078 US-U II (pp. 1-23).
Office Action dated Mar. 4, 2020 fo U.S. Appl. No. 15/678,710, 3376 US-U II (pp. 1-14).
Office Action dated Sep. 3, 2019 for U.S. Appl. No. 15/613,578, 4078 US-U II (47631-265806), (pp. 1-20).

\* cited by examiner

VEHICLE SEAT

PRIORITY CLAIM

This application claims priority under 35 U.S.C. § 119(e) to U.S. Provisional Application Ser. No. 62/384,357, filed Sep. 7, 2016, which is expressly incorporated by reference herein.

BACKGROUND

The present disclosure relates to occupant supports including a sensor system. More particularly, the present disclosure relates to occupant supports for use in a vehicle and including one or more sensors configured to sense physiological characteristics of an occupant supported by the occupant support.

SUMMARY

According to the present disclosure, an occupant support system in accordance with the present disclosure is adapted for use in a vehicle. The occupant support system includes a seat bottom and a seat back. The seat back is coupled to the seat bottom and arranged to extend in an upward direction away from the seat bottom.

In illustrative embodiments, the occupant support system includes a sensor system and a control system. The sensor system is configured to obtain occupant-body signals associated with physiological characteristics and behavioral signals associated with behavioral characteristics of an occupant of the occupant support system. The control system is configured to receive and process the occupant-body signals and the behavioral signals to determine occupant health data and occupant state data such as, for example, comfort and stress. The control system analyzes the data to recommend activating vehicle systems and lifestyle amenities to improve the comfort and wellbeing of the occupant.

In illustrative embodiments, the control system is configured to monitor the occupant and the vehicle systems to determine the effect of activating the vehicle systems and the lifestyle amenities and to learn the occupant's preferences. The occupant health data, occupant state data, and learned occupant behaviors are associated in a unique occupant data profile associated with a single occupant. The control system adds information and trends to the unique occupant data profile over time to improve its occupant comfort and wellness recommendations.

In illustrative embodiments, the occupant support system is configured to determine a health score of the occupant based on the occupant health data and the occupant state data. The health score is normalized using specific occupant conditions and data as well as by comparing the occupant's data with that of occupant data from other vehicles.

Additional features of the present disclosure will become apparent to those skilled in the art upon consideration of illustrative embodiments exemplifying the best mode of carrying out the disclosure as presently perceived.

BRIEF DESCRIPTION OF THE DRAWINGS

The detailed description particularly refers to the accompanying figures in which.

DETAILED DESCRIPTION

Figure 1:
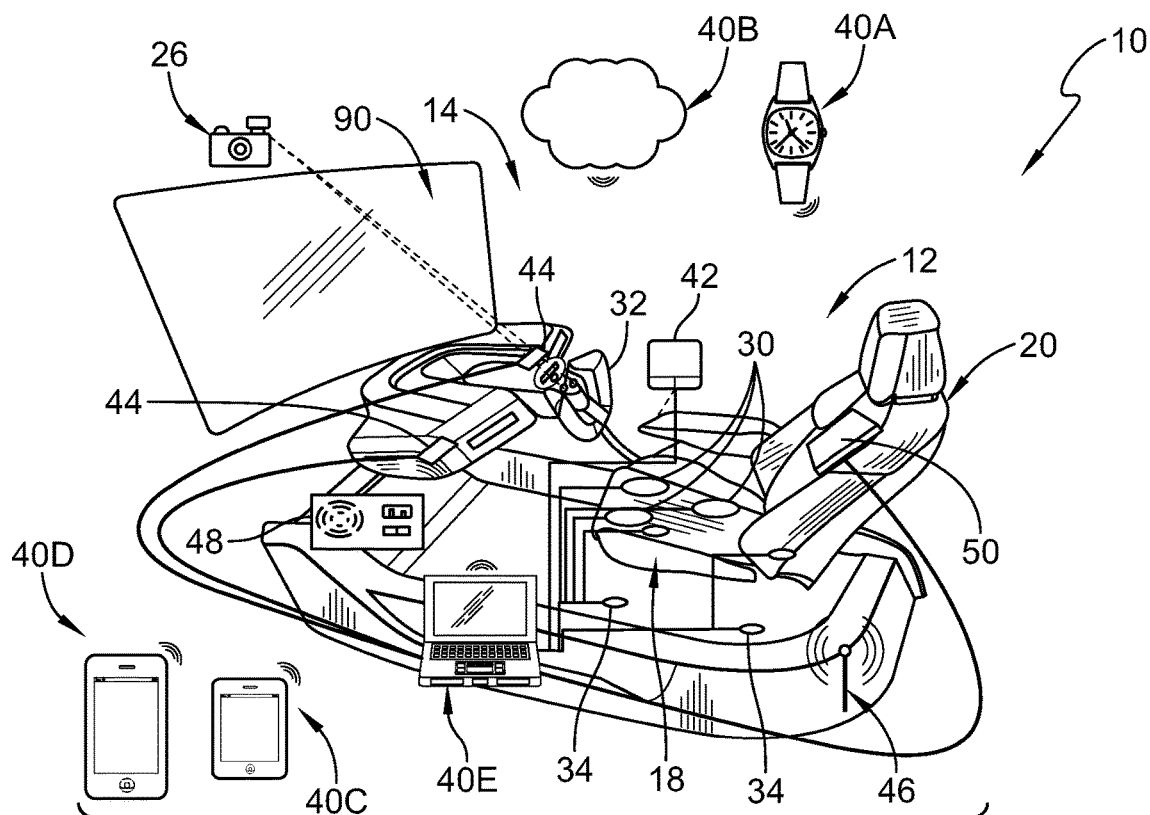
FIG. 1 is a perspective and diagrammatic view of an occupant support system in accordance with the present disclosure showing that the occupant support system is adapted for use in a vehicle and that the occupant support system includes a sensor system including a plurality of sensors configured to measure physiological and behavioral data of an occupant of the occupant support system.
Figure 5:
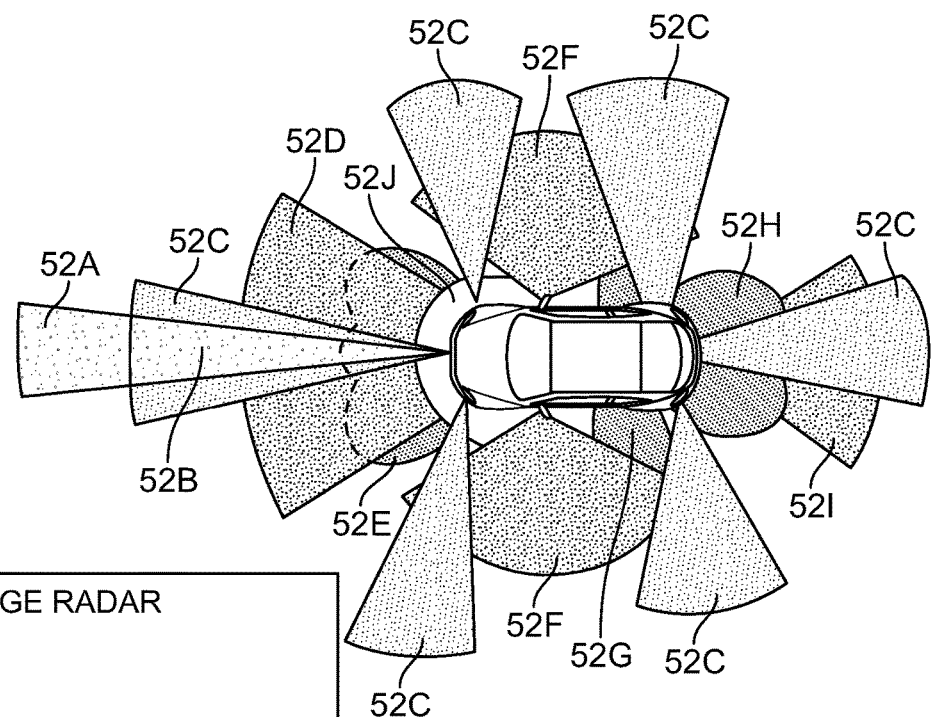
FIG. 5 is a top plan and diagrammatic view of a vehicle adapted to include the occupant support system and showing that the sensor system included in the occupant support system further includes a long-range radar, a LIDAR system, an optical camera, and a short-/medium-range radar.
Figure 6:
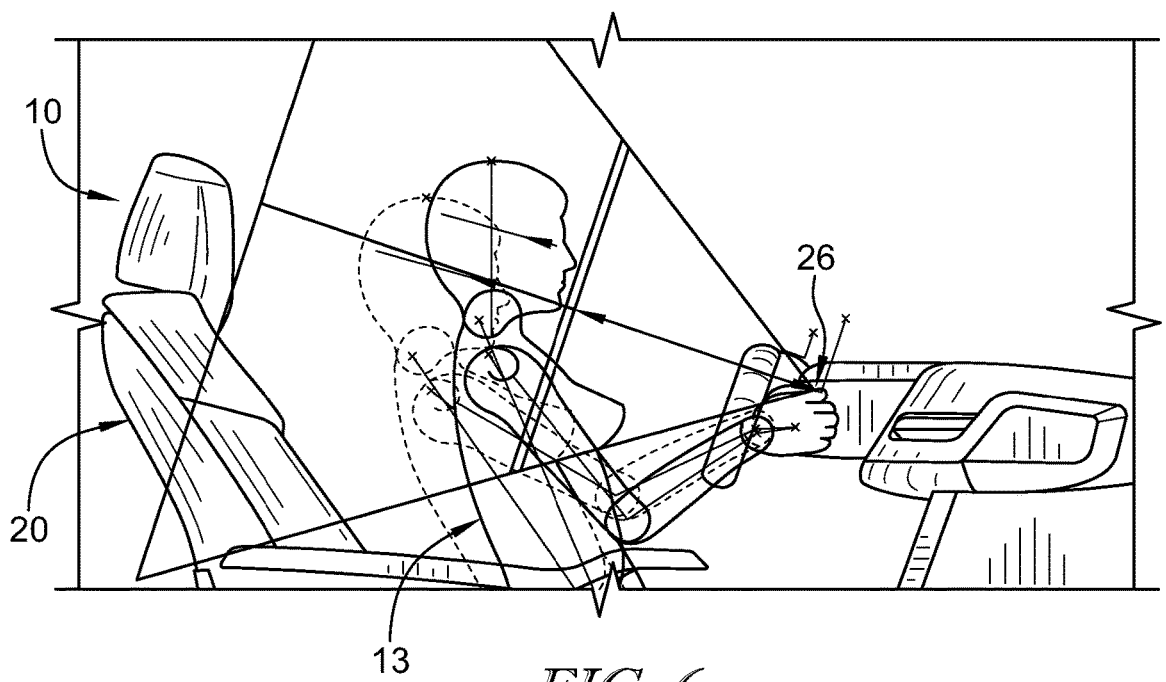
FIG. 6 is a diagrammatic view of the occupant support system of FIG. 1 showing an occupant positioned near the optical camera system included in the sensor system and suggesting that the optical camera system is configured to view the occupant's face and shoulders and further configured to focus on the occupant when the occupant is in different sitting arrangements and distances relative to the optical camera system.

An occupant support system 10 in accordance with the present disclosure is adapted for use in a vehicle 11 as shown in FIGS. 1, 5, and 6. Occupant support system 10 is configured to support an occupant 13 in vehicle 11 and to monitor health and behavior characteristics of occupant 13 to generate recommendations to improve occupant's wellness and/or comfort. For example, occupant support system 10 may recommend activating a massage system 86 to improve occupant's comfort and blood flow or recommend a coffee break if occupant 13 is likely to be drowsy. Over time, occupant support system 10 obtains more and more occupant health data and occupant feedback to improve its recommendations and, thereby, improve occupant wellness and/or comfort.

Figure 2:
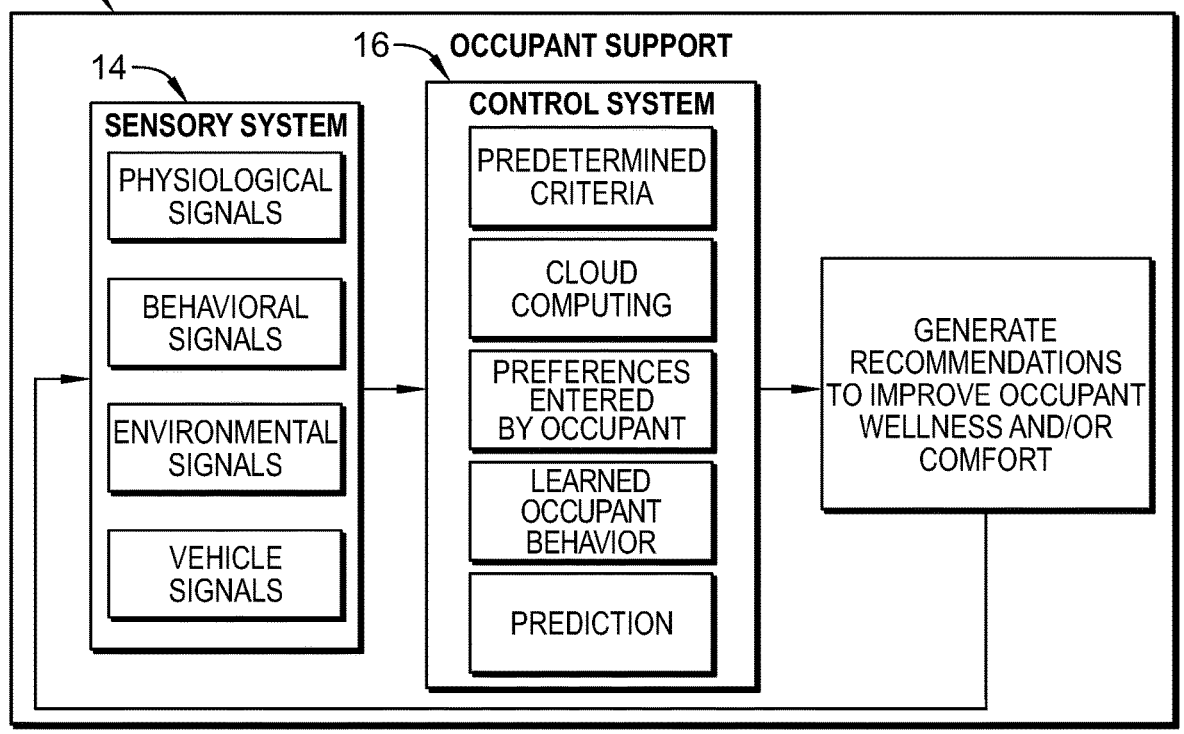
FIG. 2 is a diagrammatic view of the occupant support system of FIG. 1 showing that the occupant support system includes the sensor system and a control system, the sensor system is configured to detect one or more of occupant physiological signals, occupant behavioral signals, environmental signals, and vehicle signals, and the control system is configured to analyze the signals to generate occupant health data, occupant state data, and recommendations to improve a wellness and/or comfort of the occupant based on the occupant health data and/or the occupant state data.

Occupant support system 10 includes a seat 12, a sensor system 14, and a control system 16 as shown in FIGS. 1 and 2. Seat 12 includes a seat bottom 18 coupled to a floor of vehicle 11 and a seat back 20 that extends upwardly away from seat bottom 18. Sensor system 14 includes a plurality of sensors configured to measure occupant physiology, occupant behavior, surrounding environment information, and vehicle information as suggested in FIGS. 3-8. Control system 16 determines occupant health data indicative of physiological and behavioral characteristics of occupant 13 and occupant state data indicative of a state of occupant 13 based on the signals from sensor system 14 as suggested in FIG. 11A. Control system 16 analyzes the occupant health data and occupant state data and determines recommendations for improving the wellness and/or comfort of occupant 13 as suggested in FIG. 11B.

Based on at least one of the occupant health data and the occupant state data, control system 16 identifies one or more of a plurality of vehicle systems 78 suitable to change at least one physiological characteristic or behavioral characteristic of occupant 13. For example, control system 16 may determine that a sound system 80 is suitable for changing a heart rate 102 of occupant 13. Control system 16 recommends to occupant 13 to activate the vehicle system(s) 78 based on the occupant health data and the occupant state data.

Vehicle system 78 may be activated automatically by control system 16 or manually by occupant 13 in response to the recommendation. Alternatively, occupant 13 may activate a different vehicle system 78. Control system 16 monitors which vehicle system(s) 78 is activated and the effect on the occupant health data and occupant state data. Control system 16 associates the selected vehicle system 78, the occupant health data, and the occupant state data in a unique occupant data profile to learn occupant preferences and effective recommendations. Future recommendations may be based on the occupant's preferences and effective recommendations such that they are more tailored to occupant 13 over time.

Recommendations may also include external activities and therapies. For example, control system 16 may determine that occupant 13 is or will likely be drowsy and recommend a coffee break. In another example, control system 16 is aware of a medication schedule of occupant 13 and recommends taking the medication at a scheduled time.

Control system 10 determines a health score of occupant 13 in some embodiments. The health score is determined based on one or more of the occupant health data, occupant state data, and medical conditions known to control system 16. Control system 16 is configured to display the health score for occupant's information as suggested in FIG. 11C. In one example, the health score is normalized by comparing it with health scores of occupants of other vehicles through cloud computing.

Advanced analytics may be used for identifying correlations between occupant 13 and the events experienced to suggest action using recommendations. Suggested actions result from advanced analytics of similar occupant profiles on the cloud with similar situational data, for example a pool of participant data that has already experienced the situation this particular occupant is experiencing, to make recommendations to this particular occupant 13 in some embodiments.

Occupant support system 10 includes seat 12, sensor system 14, and control system 16 as shown in FIGS. 1 and 2. Seat 12 is configured to support occupant 13 in vehicle 11. Sensor system 14 measures occupant physiology, occupant behavior, surrounding environment information, and vehicle information. Control system 16 analyzes the signals and determines recommendations for improving the wellness and/or comfort of occupant 13 based on the analyzed signals.

Seat 12 includes seat bottom 18 and seat back 20 as shown in FIG. 1. Seat bottom 18 is configured to move relative to the floor of the vehicle. Seat back 20 is configured to move relative to seat bottom 18 such that seat 12 is configured to move between an upright position and a folded-forward position. Seat 12 includes a plurality of sensors included in sensor system 14. In the illustrative embodiment, seat 12 is a driver side seat 12.

Sensor system 14 includes the plurality of sensors as shown in FIGS. 3-10. Measurements from sensor system 14 are used to determine occupant health data and occupant state data as suggested in FIG. 3.

Figure 3:
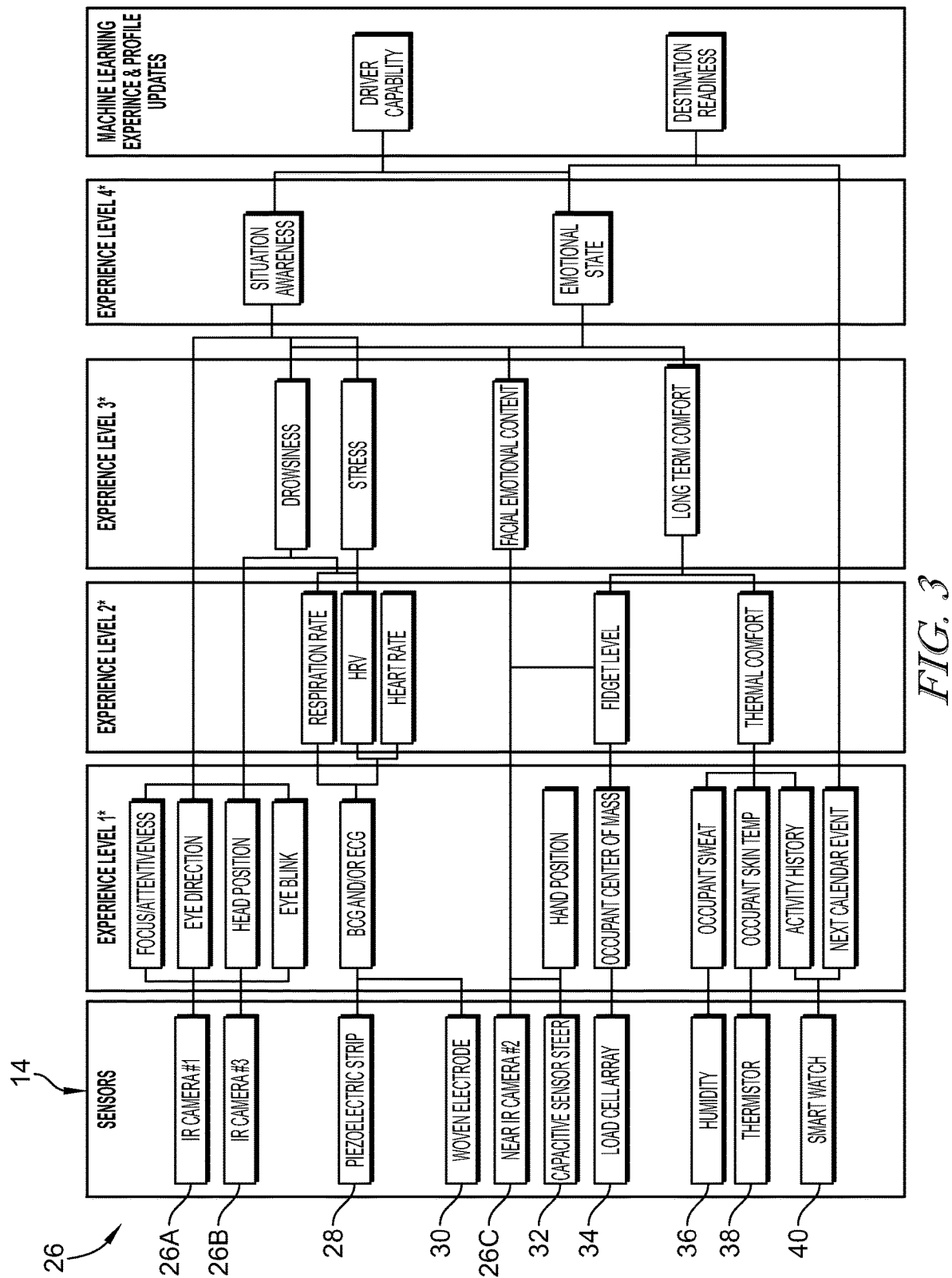
FIG. 3 is a diagrammatic view of the sensor system included in the occupant support system and a plurality of experience levels of the occupant that may be determined by the control system based on the signals received from the sensor system.
Figure 4:
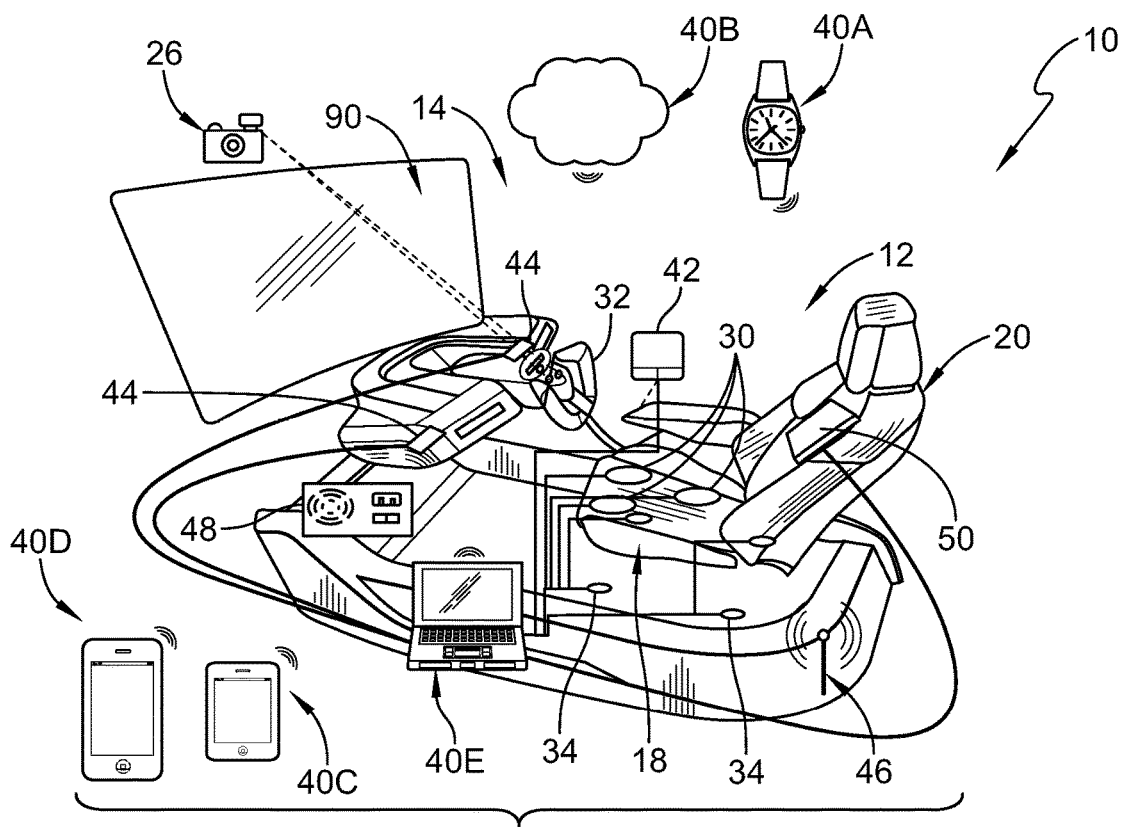
FIG. 4 is a perspective and diagrammatic view of the occupant support system similar to FIG. 1 showing that the sensor system included in the occupant support system includes a plurality of sensors for measuring physiological, behavioral, and environmental signals, the sensor system including an optical camera system, cloud analytics, external input devices such as a smart watch, smart phone, and tablet, a control board, a touch pad, an infrared emitter, an electrode, a piezoelectric sensor, a humidity sensor, a temperature sensor, a capacitive sensor, a load cell, and an oximetry sensor.

Sensor system 14 includes optical camera system 26, a piezoelectric sensor 28, an electrode 30 (i.e. woven electrode), a capacitive sensor 32, a load cell(s) 34, a humidity sensor 36, a thermistor 38, and smart devices 40 such as, for example, a smart watch 40A, cloud computing 40B, a smart phone 40C, a tablet 40D, and a personal computer 40E as shown in FIGS. 3 and 4. Thermistor 38 is configured to detect occupant temperature, cabin temperature, and outside temperature. Smart devices 40 communicate with occupant support system 10 via Bluetooth in some embodiments and may provide data in real-time when occupant 13 sits in occupant support system 10. Sensor system 14 further includes touch pad 42, control board 44 input devices, an accelerometer, a volatile organic compound sensor, an electrically-activated polymer sensor, and an air particulate sensor.

Sensor system 14 further includes a plurality of vehicle and environmental sensors 52 as shown in FIG. 5. Vehicle and environmental sensors 52 include a long-range RADAR, LIDAR, an optical camera, and short-/medium-range RADAR. Vehicle and environmental sensors 52 include vehicle to vehicle communication devices and vehicle to infrastructure communication devices in some embodiments.

A plurality of zones can be sensed with the vehicle and environmental sensors 52 as suggested in FIG. 5. The zones may include for example, an adaptive cruise control zone 52A; emergency braking, pedestrian detection, and collision avoidance zone 52B; environment mapping zones 52C; traffic sign recognition and lane departure warning zone 52D; traffic alert zone 52E; digital side mirror and surround view zones 52F; blind spot detection zone 52G; rear collision detection zone 52H; park assist, surround view, and rear view mirror zone 52I; and park assist zone 52J.

Figure 8:
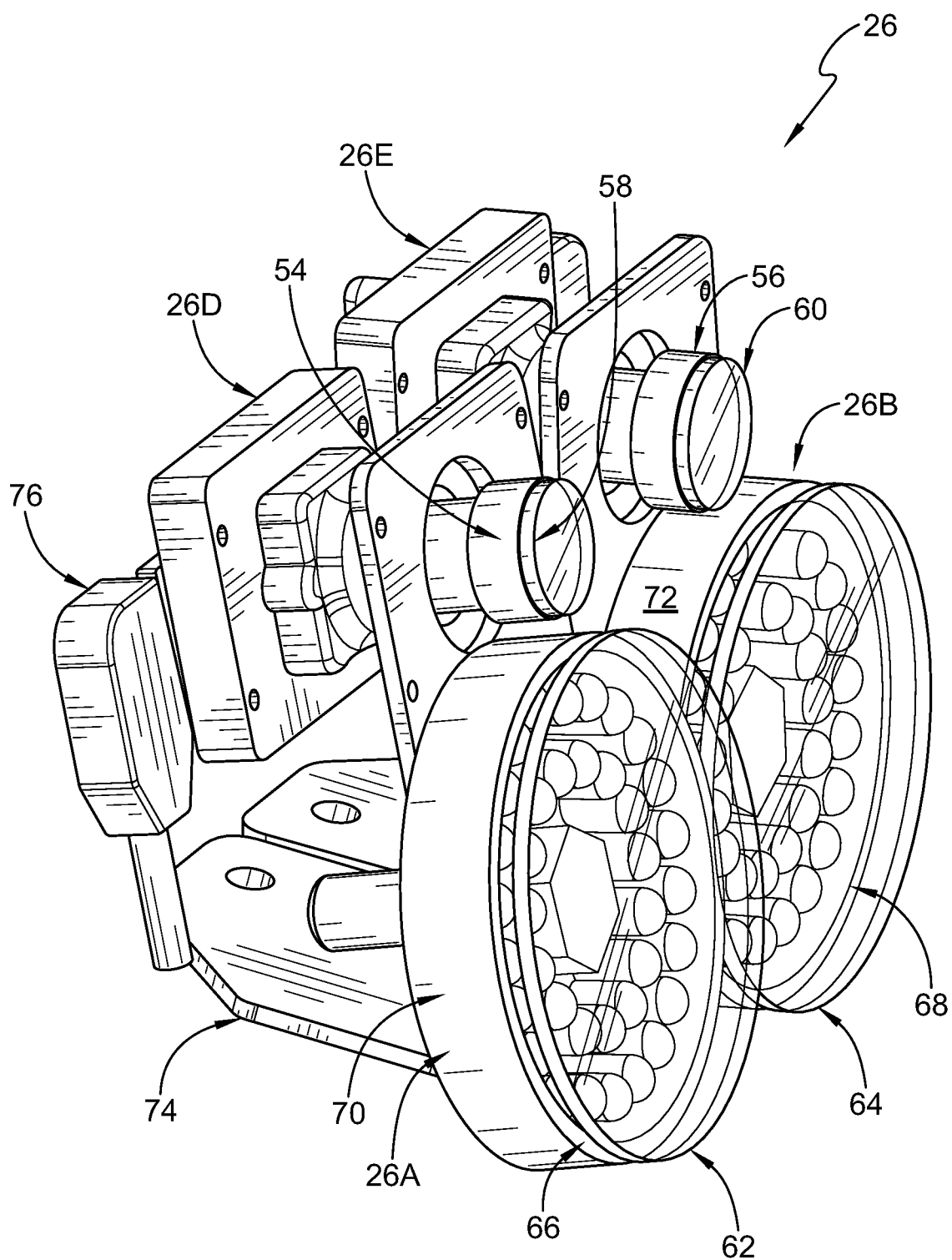
FIG. 8 is a perspective view of the optical camera system included in the sensor system showing that the optical camera system includes a first visible light camera, a second visible light camera, a first infrared camera, and a second infrared camera.

Optical camera system 26 of sensor system 14 include a first infra-red camera 26A, a second infrared camera 26B, a third infrared camera 26C, a first visible light camera 26D, and a second visible light camera 26E as shown in FIGS. 3, 4, and 8. Infrared cameras 26A, 26B, 26C include near-field and far-field infrared cameras. In some embodiments, sensor system 14 further includes a fluid pressure sensor. As shown in FIG. 4, occupant support system 10 further includes a wireless router 46, a power supply 48, and an electronic control unit 50.

Figure 7:
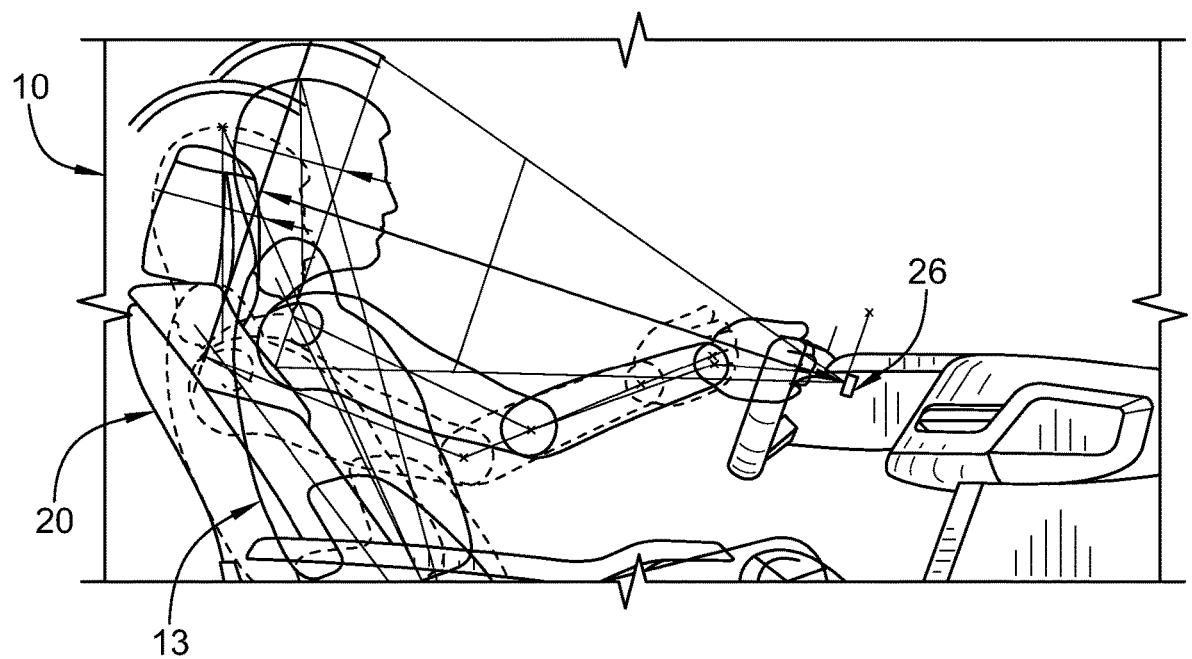
FIG. 7 is a view similar to FIG. 6 showing that the occupant is positioned far away from the optical camera system included in the sensor system and suggesting that the optical camera system is configured to view the occupant's face and shoulders.

Optical camera system 26 is configured to change a field of view to detect occupant 13 when occupant 13 is in a plurality of positions as suggested in FIGS. 6 and 7. In one example, optical camera system 26 uses a camera with a 3.6 millimeter diameter lens 54 to view occupant 13 as little as about 350 millimeters away from optical camera 26 with a field of view of about 69 degrees as suggested in FIG. 6. Optical camera system 26 further includes a camera with an 8.0 millimeter diameter lens 56 to view occupant 13 as far as about 850 millimeters away from optical camera 26 with a field of view of about 34 degrees as suggested in FIG. 7.

One embodiment of optical camera system 26 is shown in FIG. 8. Optical camera system 26 is located in a steering column of vehicle 11 as suggested in FIG. 4. Optical camera system 26 includes first visible light camera 26D, second visible light camera 26E, first infra-red camera 26A, and second infrared camera 26B. Each visible light cameras 26D, 26E include a lens 54, 56 and a filter 58, 60 respectively. Lens 54 is a 3.6 millimeter lens and lens 56 is an 8.0 millimeter lens. Infra-red cameras 26A, 26B include diffusers 62, 64 filters 66, 68, and guides 70, 72 respectively. Optical camera system 26 further includes a mount 74 and a USB port 76.

Figure 9:
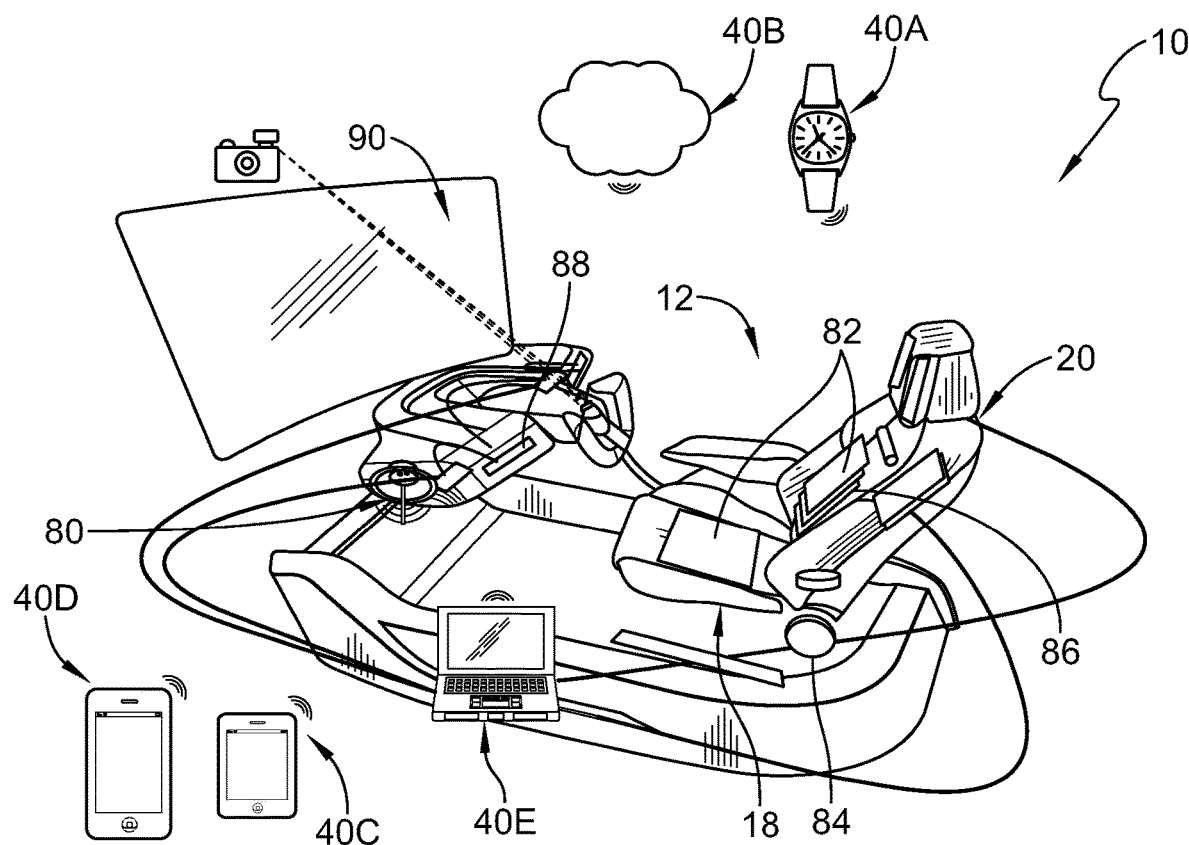
FIG. 9 is view similar to FIG. 1 showing that the occupant support system includes a plurality of vehicle systems adapted to provide informational, tactile, visual, aural, olfactory, and thermal feedback to the occupant to provide health information and/or therapies for the occupant.
Figure 10:
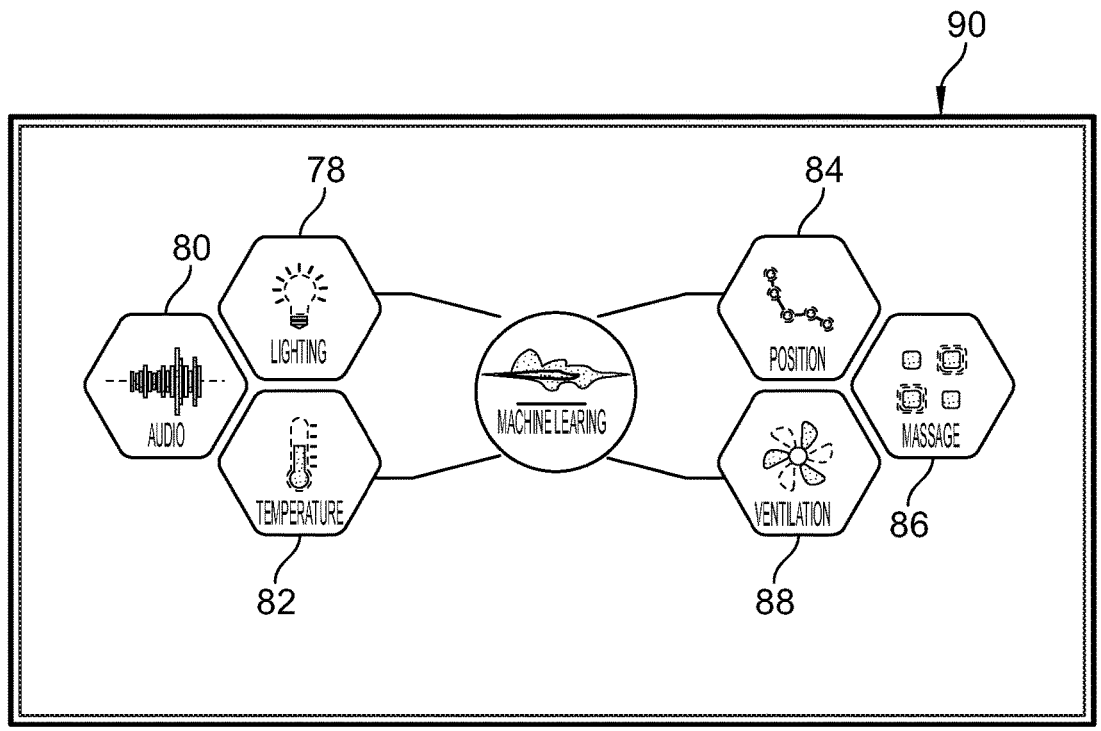
FIG. 10 is a diagrammatic view of a display included in the occupant support system showing that the vehicle systems included in the occupant support system include an audio system, a lighting system, a temperature system, an occupant position system, a ventilation system, and a massage system.

Occupant support system 10 includes a plurality of vehicle systems 78 (sometimes called outputs) as shown in FIGS. 9 and 10. Vehicle systems 78 provide informational, tactile, visual, audial, olfactory, and thermal feedback to occupant 13. Vehicle systems 78, alone or in combination, may be activated to apply a variety of therapies to occupant 13 to change at least one physiological characteristic or behavioral characteristic of occupant 13.

Vehicle systems 78 include a lighting system 81, an audio sound system 80, a temperature system 82, a position system 84, a massage system 86, a ventilation system 88, a visual display 90, smart devices 40A, 40B, 40C, 40D, 40E, and optical camera system 26 as shown in FIGS. 9 and 10. Position system 84 includes adjustable seat bottom 18 and adjustable seat back 20. Temperature system 82 includes a heating and/or cooling system included in seat 12.

Figure 11A:
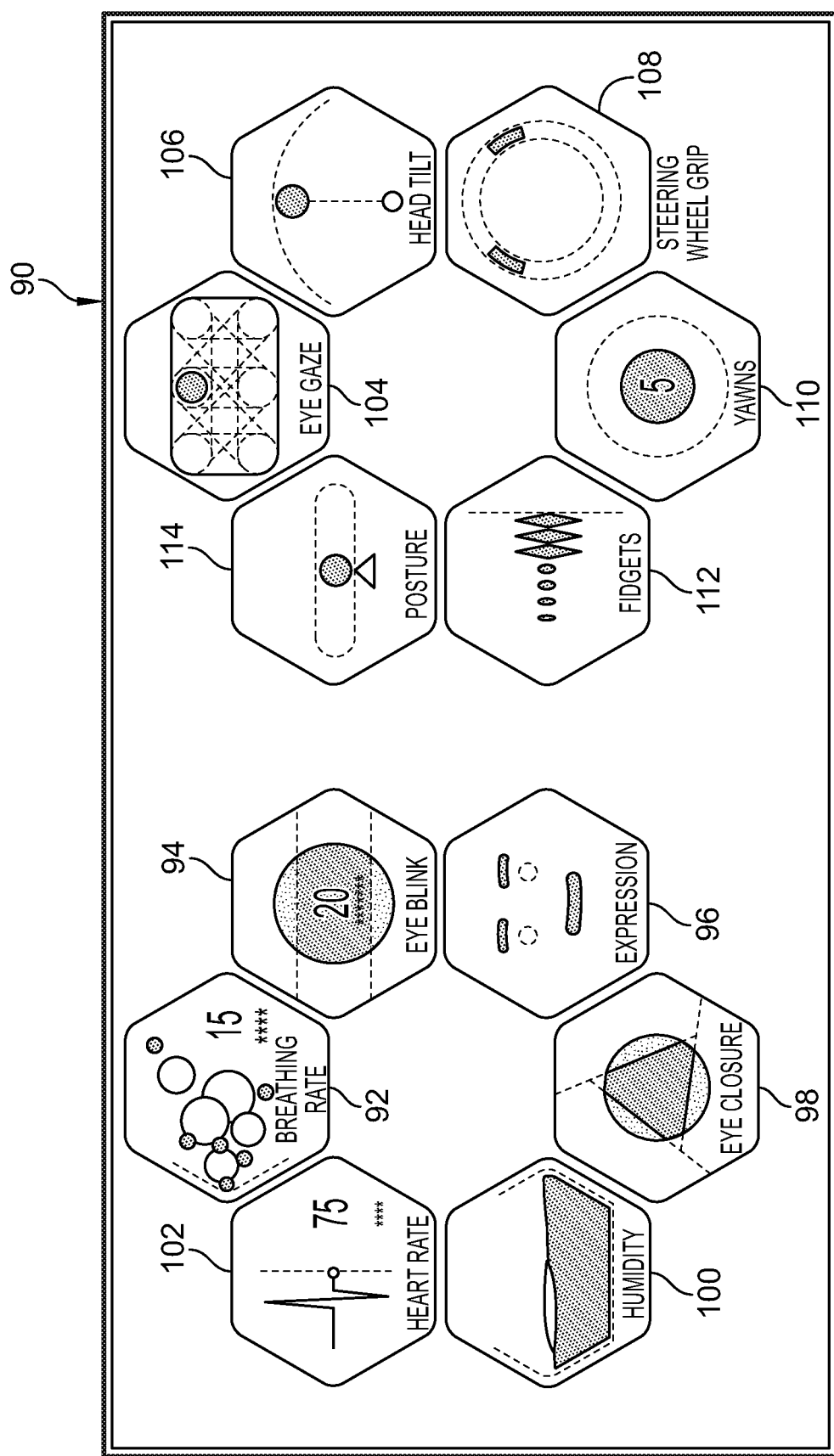
FIG. 11A is a diagrammatic view of the display included in the occupant support system showing occupant health data indicative of physiological and behavioral characteristics of the occupant.
Figure 11B:
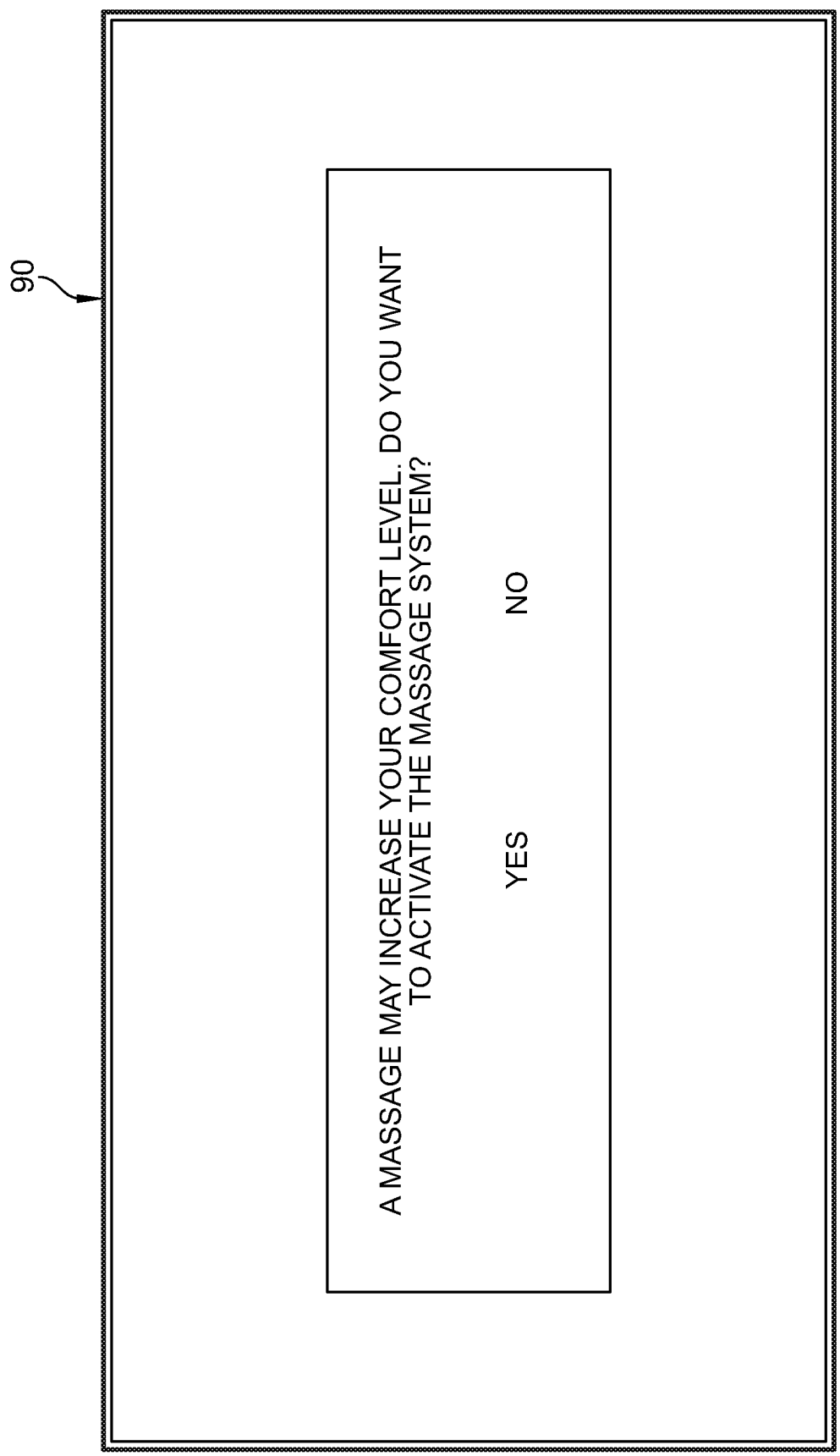
FIG. 11B is a diagrammatic view of the display included in the occupant support system showing that the occupant support system recommends activating vehicle systems to improve occupant wellness or comfort.

Control system 16 determines occupant health data and occupant state data based on the signals generated by sensor system 14 as suggested in FIGS. 3 and 11A. Control system 16 determines data based on different experience levels as shown in FIG. 3. Occupant health data and occupant state data are provided in real-time. FIG. 3 provides one example of the signals and data used to determine the data of experience levels 1-4 and the machine learning and profile update level. Other examples of determining data based on different signals and data are within the scope of this disclosure and a number of examples are provided herein.

Control system 16 is configured to determine occupant focus, occupant eye direction, occupant head position, an eye blink rate 94 of occupant 13, a BCG or ECG (electrocardiogram) of occupant 13, a hand position of occupant 13, a center of mass of occupant 13, occupant sweat level, occupant skin temperature, an activity history of occupant 13, and a next calendar event of occupant 13 in experience level 1. Occupant focus, occupant eye direction, occupant head position, and the eye blink rate 94 of occupant 13 are determined based on signals from the optical camera system 26. BCG or ECG (electrocardiogram) of occupant 13 is determined based on signals from the piezoelectric sensor 28 and the electrode 30. The hand position of occupant 13 is based on signals from the capacitive sensor 32 which determines steering wheel grasp. The center of mass of occupant 13 is based on signals from the load cell(s) 34. The occupant sweat level is based on signals from the humidity sensor 36. The occupant skin temperature is based on signals from the thermistor 38. The activity history of occupant 13 and a next calendar event of occupant 13 are based on signals from the smart devices 40.

A respiration rate of occupant 13, heart rate variation (HRV), and heart rate 102 of occupant 13 are based on the ECG data determined in level 1 as shown in FIG. 3. Fidget level 112 of occupant 13 is based on signals from optical camera system 26 and capacitive sensor 32 as well as occupant center of mass data determined in experience level 1. The thermal comfort of occupant 13 is based on occupant sweat level, occupant skin temperature, and activity history data determined in experience level 1.

A drowsiness of occupant 13, stress of occupant 13, facial emotional content of occupant 13, and long term comfort of occupant 13 are determined in experience level 3 as shown in FIG. 3. Drowsiness of occupant 13 is based on one or more of focus of occupant 13, eye direction of occupant 13, head position of occupant 13, eye blink rate 94 of occupant 13, respiration rate of occupant 13, and HRV of occupant 13 determined in experience levels 1 and 2. Stress of occupant 13 is based on respiration rate and HRV data determined in experience level 2. The facial emotional content of occupant 13 is based on signals from optical camera system 26 and fidget level data determined in experience level 2.

Long term comfort of occupant 13 is based on fidget level 112 and thermal comfort data determined in experience level 2. Hand and leg position feed into facial content, fidget level 112, thermal comfort, long-term comfort, and emotional state. Biometric and/or wearables including smart devices 40 include activity history with feedback from sweat and skin temperature experiences, with a next calendar event connection to devices 40.

A situational awareness of occupant 13 and an emotional state of occupant 13 are determined in experience level 4 as shown in FIG. 3. Situational awareness of occupant 13 is determined based on one or more of focus of occupant 13, eye direction 104 of occupant 13, head position 106 of occupant 13, eye blink rate 94 of occupant 13, respiration rate of occupant 13, drowsiness, stress, facial emotional content, and long term comfort data determined in experience levels 1, 2, and 3. Emotional state of occupant 13 is based on one or more of drowsiness, stress, facial emotional content, and long term comfort of occupant 13 data determined in experience level 3.

Machine learning experience level and profile updates includes driver capability and destination readiness as shown in FIG. 3. Driver capability is based on situation awareness and emotional state data determined in experience level 4. Destination readiness is based on emotional state and next calendar event data determined in experience levels 1 and 4.

In the illustrative embodiment, control system 16 is configured to generate instructions to display occupant health data, for example, on display 90 for occupant information as suggested in FIG. 11A. The occupant health data is displayed in geometric patterns and includes indicia of the health data and numeric values or graphical values associated with the occupant health data. Breathing rate 92, eye blink rate 94, the facial expression 94, eye closure level 96, humidity 100 around occupant 13, heart rate 102, eye gaze 104, head tilt 106, steering wheel grip 108, yawn rate 110, fidget level 112, and posture 114 of occupant 13 are displayed in FIG. 11A.

Control system 16 is configured to determine occupant state data based on the occupant health data and generate instructions to display the occupant health data to occupant 13 as suggested in FIGS. 12-16. A plurality of states are shown and described, however other occupant states are contemplated. Occupant state data includes numerical values indicative of the severity of the state in some embodiments. In some embodiments, occupant state data is determined to be normal, low, or high based on predetermined criteria.

Control system 16 is configured to receive the occupant-body signals and the behavioral signals from sensor system 14 and determine occupant health data indicative of physiological characteristics and behavioral characteristics of occupant 13 based on the occupant-body signals and the behavioral signals. Control system 16 further determines occupant state data indicative of a state of occupant 13 based on the occupant health data.

Control system 16 identifies a vehicle system 78 configured to change at least one physiological characteristic or behavioral characteristic of the occupant based on at least one of the occupant health data and the occupant state data. In one example, vehicle system 78 is determined based on occupant health data, occupant state data, and predetermined criteria. Control system 16 recommends that occupant 13 activates vehicle system 78 to improve the wellness or comfort level of occupant 13 as suggested in FIG. 11B.

Control system 16 activates a vehicle system 78 based on at least one of the occupant health data, the occupant state data, and input from the occupant. Activated vehicle system 78 may be the same or different than the recommended vehicle system 78. For example, control system 16 recommends activating massage system 86, but activates temperature system 82 based on occupant input. In another example, control system 16 recommends activating massage system 86 and activates massage system 86 based on occupant input or occupant health data.

Control system 16 is configured to associate activation of vehicle system 78 with the occupant health data and the occupant state data in a unique occupant data profile. The unique occupant data profile is specific to one occupant and more information is added to unique occupant data profile over time to increase the accuracy and effectiveness of the recommendations made by control system 16. Control system is configured to identify occupant 13 based on at least one of input from occupant 13 and the occupant health data.

Data associated in unique occupant data profile includes occupant height, weight, sex, and age data. Such data may be entered manually by occupant 13, by smart device 40, and/or by an internet connection. Unique occupant data profile further includes a medical history including medical conditions of occupant 13. A completion level of the unique occupant data profile may be depicted by shading of silhouette from foot to head. No shading corresponds to an incomplete profile and full shading corresponds to a complete profile.

By associating associate activation of vehicle system 78 with the occupant health data and the occupant state data in the unique occupant data profile, control system 16 learns occupant preferences and behaviors over time. If the recommended vehicle system 78 is activated, control system 16 learns that occupant 13 agrees with that recommendation while occupant 13 exhibits that occupant health data and occupant state data. If the recommended vehicle system 78 is not activated and instead, another vehicle system 78 is activated, control system 16 learns that occupant 13 prefers the other vehicle system 78 while occupant 13 exhibits that occupant health data and occupant state data. Control system 16 learns and improves its recommendations as the number of iterations increase.

Control system 16 is configured to determine the effectiveness of activating vehicle system 78. Control system 16 monitors and analyzes the physiological and behavioral data of occupant 13 to determine the effect of vehicle systems 78 on occupant 13. In one example, control system 16 is configured to receive supplemental occupant-body signals and supplemental behavioral signals after activating the vehicle system. Control system 16 determines supplemental occupant health data based on the supplemental occupant-body signals and the supplemental behavioral signals. Control system 16 determines supplemental occupant state data based on the supplemental occupant health data.

Control system 16 identifies a vehicle system 78 configured to change at least one physiological characteristic or behavioral characteristic of occupant 13 based on at least one of the supplemental occupant health data, the supplemental occupant state data, and the unique occupant data profile. Control system 16 activates a vehicle system 78 based on at least one of the supplemental occupant health data, the supplemental occupant state data, the unique occupant data profile, and input from occupant 13. The activated vehicle system 78 may be the same or different than the previously activated or recommended vehicle system 78.

The control system 16 is configured to associate activation of the vehicle system 78 with the supplemental occupant health data and the supplemental occupant state data in the unique occupant data profile to learn occupant behavior and preferences. Control system 16 compares the occupant health data and the supplemental occupant health data and associates changes to the occupant health data in the unique occupant data profile.

Figure 11C:
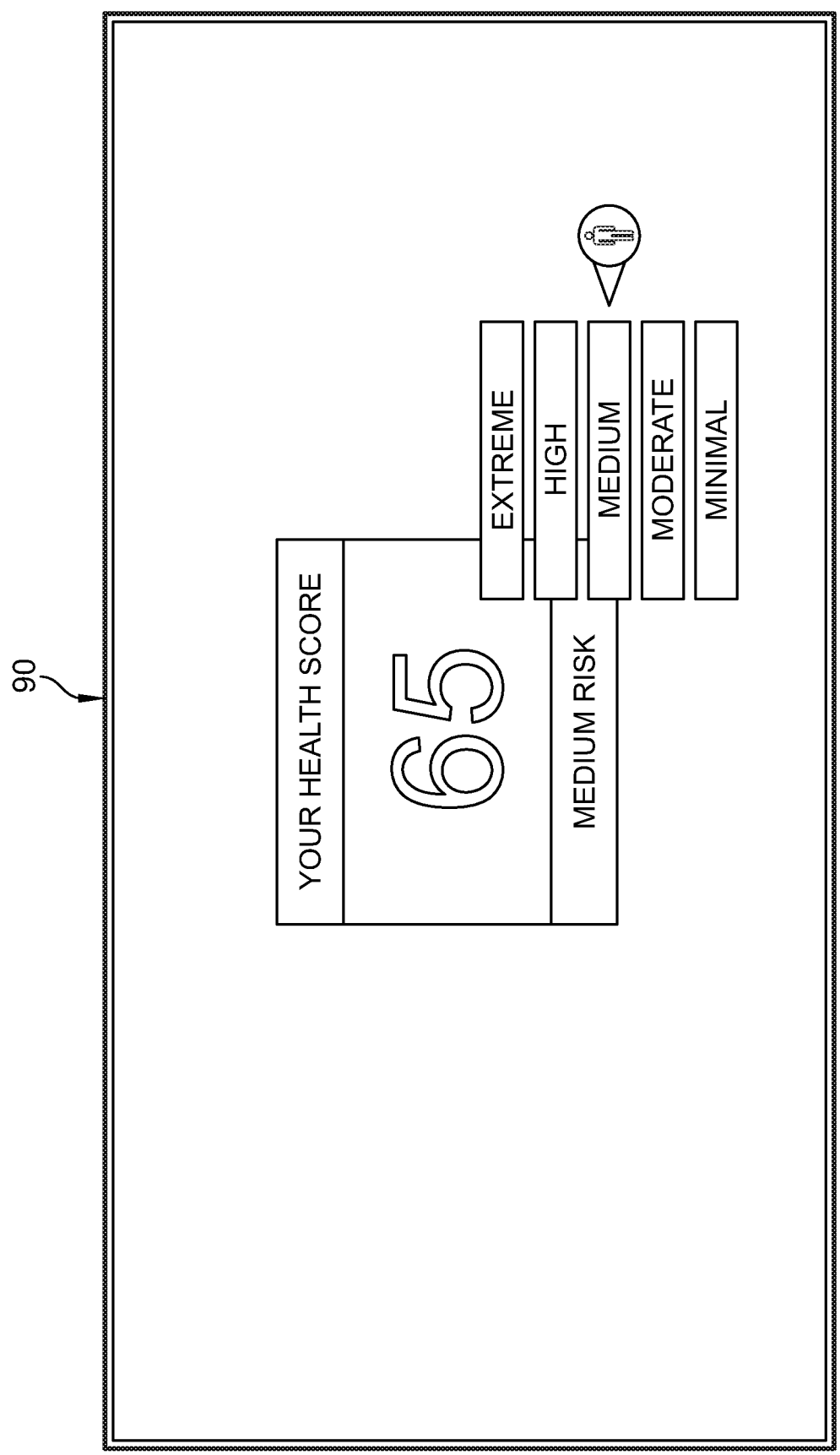
FIG. 11C is a diagrammatic view of the display included in the occupant support system showing that the occupant support system is configured to display a health score of the occupant.
Figure 12:
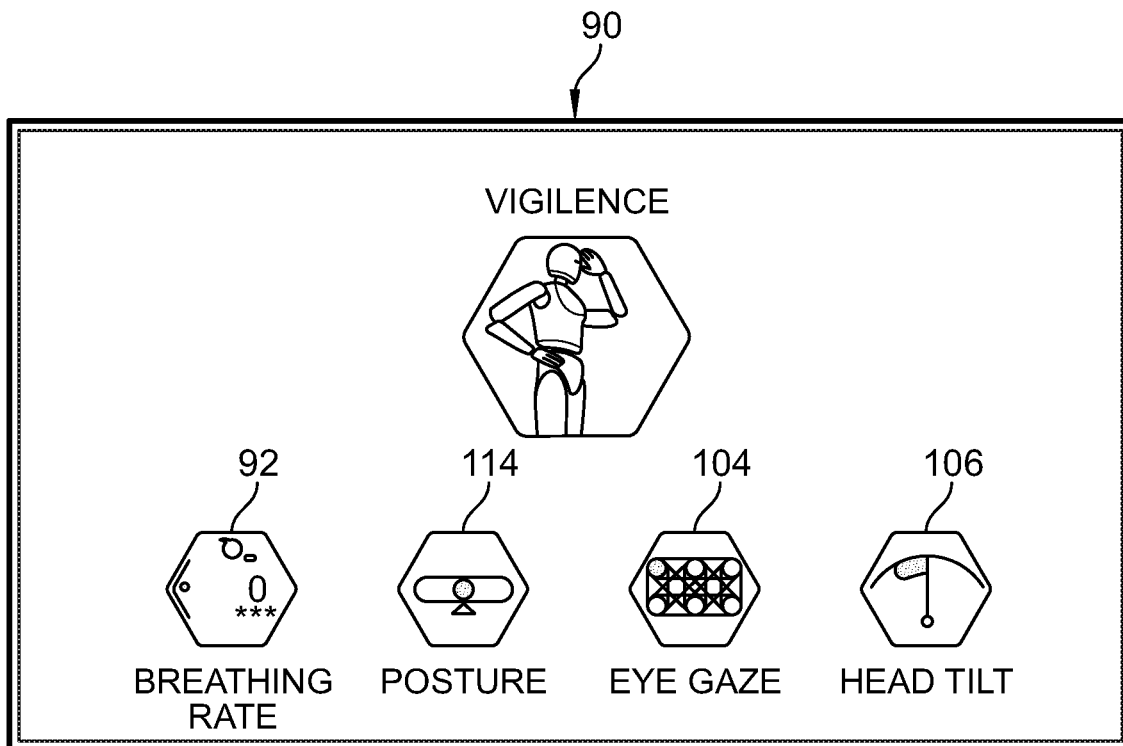
FIG. 12 is a diagrammatic view of the display included in the occupant support system showing occupant state data and, in particular, showing indicia associated with a vigilance of the occupant and suggesting that the vigilance of the occupant is based on a breathing rate of the occupant, a posture of the occupant, an eye gaze of the occupant, and a head tilt of the occupant.

Control system 16 determines a health score of occupant 13 in some embodiments, as suggested in FIG. 11C. Control system 16 is configured to receive secondary health data unique to occupant 13 from at least one of an input and an accessory device. For example, secondary health data includes a height, sex, weight, and/or age of occupant 13. Secondary health data may include a medical history and medical conditions of occupant 13 input manually or received via a smart device or over an internet connection. Control system 16 associates the secondary data with the unique occupant data profile and determine the health score of occupant 13. Control system 16 generates instructions to display the health score to occupant 13 as suggested in FIG. 11C.

In one example, the health score is based on the occupant health data, the unique occupant data profile, and predetermined criteria. In another example, the health score is based on the occupant health data, the unique occupant data profile, the secondary health data, and predetermined criteria. In some embodiments, the health score is based on cloud data of other vehicle occupants.

In some embodiments, control system 16 analyzes the occupant data over a period of time and provides a raw health score. The raw scores are tallied and compared to predetermined criteria. The raw scores are normalized for the occupant's particular occupant profile and history. The control system 16 generates instructions for outputting the health score.

Control system 16 receives schedule data indicative of scheduled events of occupant 13 from at least one of an input and an accessory device, such as, for example, smart device 40 and to prompt occupant 13 to perform an activity based on the schedule data. For example, control system 16 may remind occupant 13 of an upcoming birthday and recommend stopping for a birthday card or present. As another example, control system 16 reminds occupant 13 to take medication at a preset time.

In some embodiments, control system 16 anticipates occupant's 13 use of vehicle amenities and therapies such as, for example, vehicle systems 78. Occupant 13 is connected with occupant support system 10 via smart devices 40. Smart devices 40 provide occupant support system 10 with reminders such as reminders for meetings, birthdays, and taking medication. Control system 16 recommends external activities such as, for example, a coffee break if the occupant is about to experience drowsiness as determined based on occupant health data, occupant state data, and previous data associated in the unique occupant data profile.

In one example, the occupant state data is indicative of a vigilance of occupant 13. The vigilance of occupant 13 is based on occupant health data that includes information indicative of the respiration rate of the occupant determined from signals received from piezoelectric sensor 28 and electrode 30, posture 114 of occupant 13 determined from signals received from load cell(s) 34 and optical camera system 26, eye gaze 104 of the occupant determined from signals received from optical camera system 26, and head tilt 106 of occupant 13 determined from signals received from optical camera system 26.

In another example, vigilance is determined based on one or more of recent activities of occupant 13, audio settings of sound system 80, respiration rate 92 of occupant 13, posture 114 of occupant 13, eye gaze 104 of occupant 13, and head tilt 106 of occupant 13.

Figure 13:
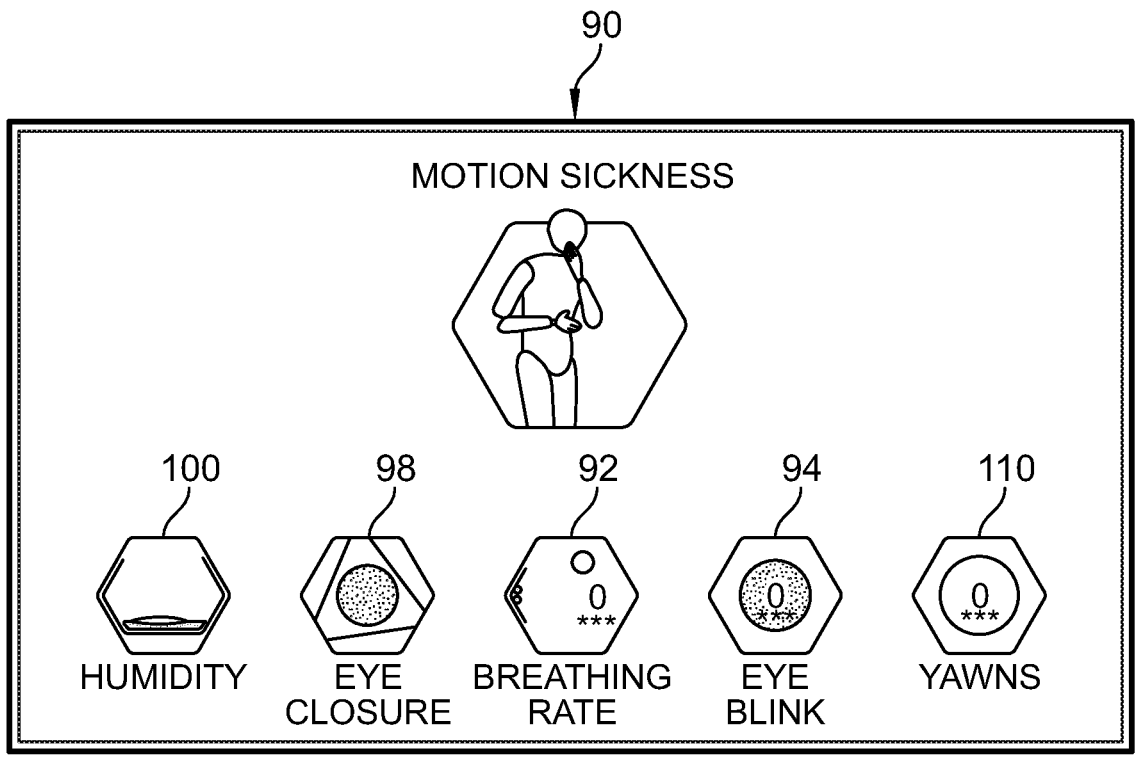
FIG. 13 is a diagrammatic view of the display included in the occupant support system showing occupant state data and, in particular, showing indicia associated with a motion sickness of the occupant and suggesting that the motion sickness of the occupant is based on humidity around the occupant, an eye closure of the occupant, a breathing rate of the occupant, an eye blink rate of the occupant, and a yawn rate of the occupant.

In another example, the occupant state data is indicative of a motion sickness of the occupant as suggested in FIG. 13. The motion sickness is based on occupant health data that includes information indicative of a humidity around occupant 13 determined from signals received from humidity sensor 36, eye closure level 98 of occupant 13 determined from signals received from optical camera system 26, eye blink rate 94 of occupant 13 determined from signals received from optical camera system 26, yawn rate 110 of occupant 13 determined from signals received from optical camera system 26, and the breathing rate 92 of occupant 13 determined from signals received from piezoelectric sensor 28 and electrode 30.

In another example, motion sickness is determined based on one or more of accelerometer data, skin color change determined by signals from optical camera system 26, humidity around occupant 13, eye closure level 98 of occupant 13, breathing rate 92 of occupant 13, eye blink rate 94 of occupant 13, and yawn rate 110 of occupant 13. In yet another example, motion sickness is determined based on humidity around occupant 13, respiration rate of occupant 13, eye closure level 98 of occupant 13, and skin color change of occupant 13.

Occupant support system 10 reduces the likelihood of motion sickness, for example, in a comfortable reading scenario. Occupant support system 10 asks occupant 13 if they would like to recline to a position that is a better fit for long-term screen-viewing. Eye gaze locations and direction may be factors used in the system assessment for optimal positioning.

Figure 14:
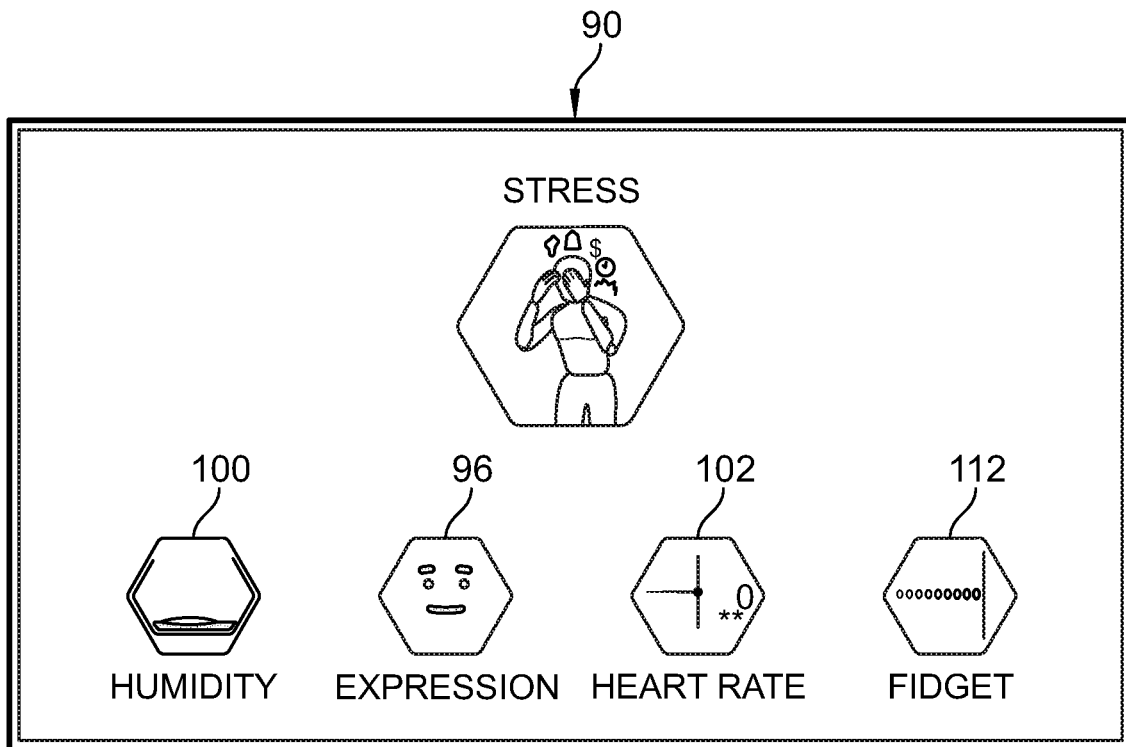
FIG. 14 is a diagrammatic view of the display included in the occupant support system showing occupant state data and, in particular, showing indicia associated with a stress of the occupant and suggesting that the stress of the occupant is based on humidity around the occupant, an expression of the occupant, a heart rate of the occupant, and a fidget level of the occupant.

In another example, occupant state data is indicative of a stress of occupant 13 as suggested in FIG. 14. The stress of occupant 13 is based on occupant health data that includes information indicative of humidity 100 around occupant 13 determined from signals received from humidity sensor 36, the facial expression 96 of occupant 13 determined from signals received from optical camera system 26, heart rate 102 of occupant 13 determined from signals received from piezoelectric sensor 28 and electrode 30, and fidget level 112 of occupant 13 determined from signals received from optical camera system 26, capacitive sensor 32, and load cell(s) 34.

In another example, stress of occupant 13 is based on one or more of the heart rate variability of occupant 13, humidity 100 around occupant 13, facial expression 96 of occupant 13, heart rate 102 of occupant 13, and fidget level 112 of occupant 13. In one example, stress of occupant 13 is based on the heart rate variability of occupant 13, humidity 100 around occupant 13, the facial expression 96 of occupant 13, and heart rate 102 of occupant 13.

Figure 15:
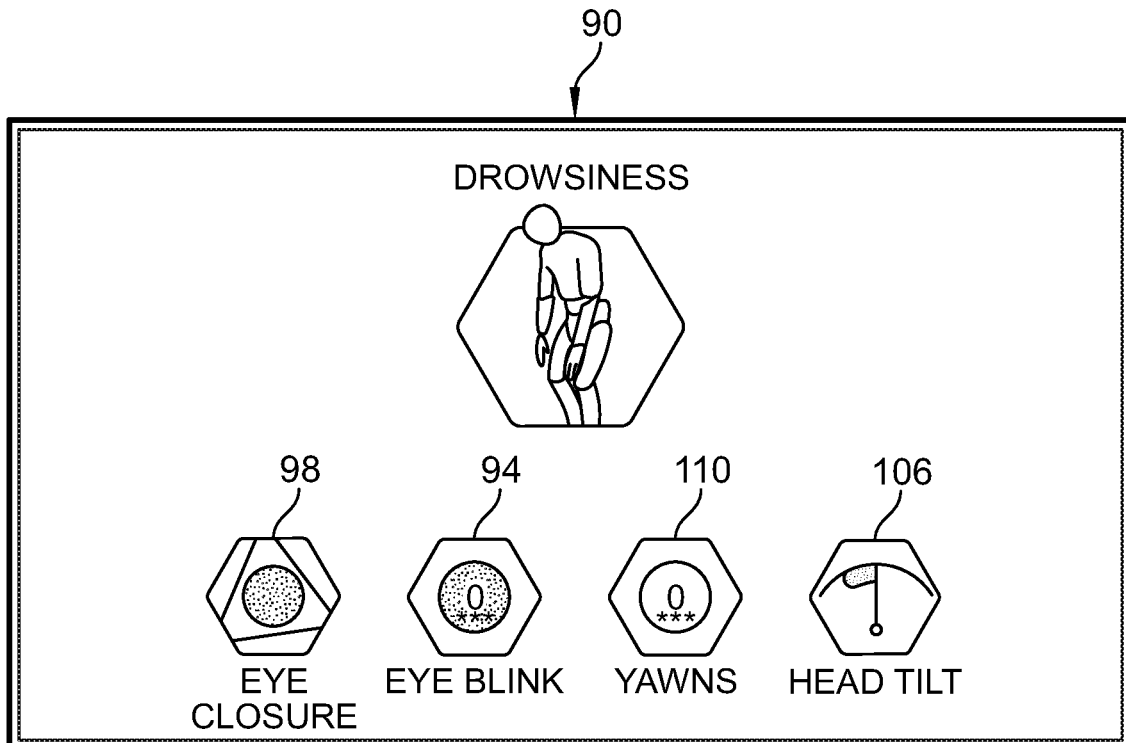
FIG. 15 is a diagrammatic view of the display included in the occupant support system showing occupant state data and, in particular, showing indicia associated with a drowsiness of the occupant and suggesting that the drowsiness of the occupant is based on an eye closure of the occupant, an eye blink rate of the occupant, a yawn rate of the occupant, and a head tilt of the occupant.

In another example, the occupant state data is indicative of a drowsiness of occupant 13 as suggested in FIG. 15. The drowsiness of occupant 13 is based on occupant health data that includes information indicative of the eye closure level 98 of occupant 13, the eye blink rate 94 of occupant 13, yawn rate 110 of occupant 13, and the head tilt 106 of occupant 13, each determined from signals received from optical camera system 26.

Figure 16:
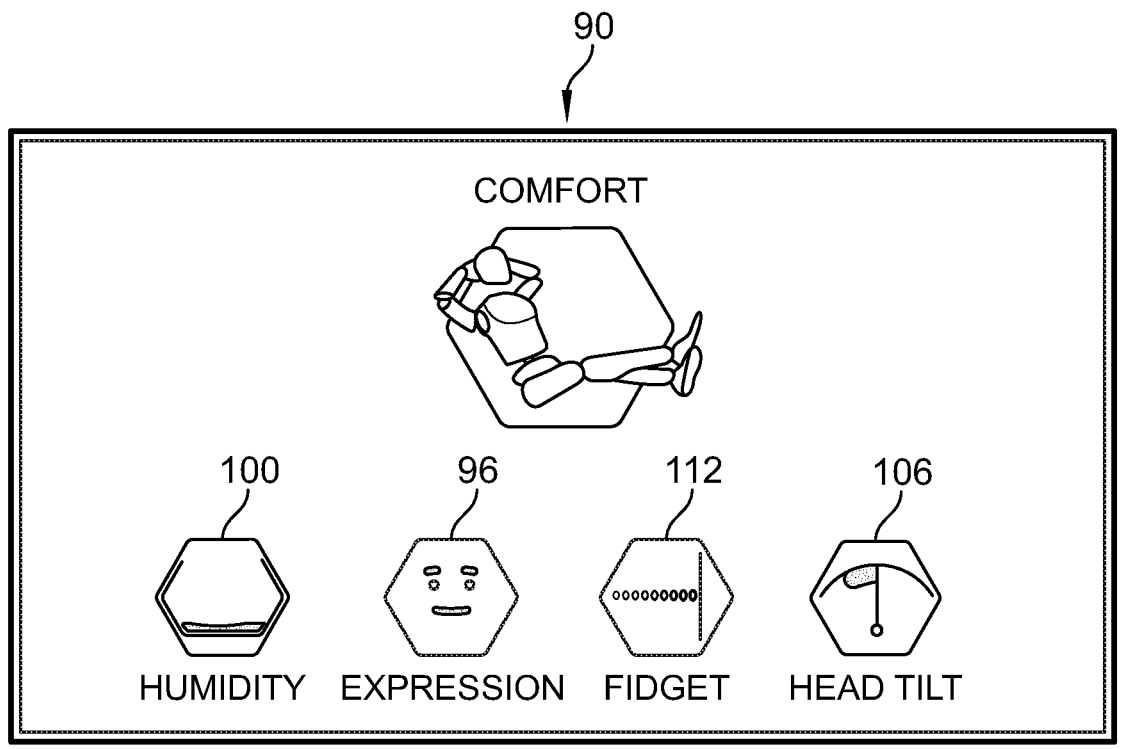
FIG. 16 is a diagrammatic view of the display included in the occupant support system showing occupant state data and, in particular, showing indicia associated with a comfort of the occupant and suggesting that the comfort of the occupant is based on humidity around the occupant, an expression of the occupant, a fidget level of the occupant, and a head tilt of the occupant.

In another embodiment, occupant state data is indicative of a comfort of occupant 13 as suggested in FIG. 16. Occupant comfort is based on occupant health data that includes information indicative of humidity 100 around occupant 13 determined from signals received from humidity sensor 36, the facial expression 96 of occupant 13 determined from signals received from optical camera system 26, fidget level 112 of occupant 13 determined from signals received from optical camera system 26, capacitive sensor 32, and load cell(s) 34, and head tilt 106 of occupant 13 determined from signals received from optical camera system 26.

In another example, occupant comfort is based on one or more of the temperature of occupant 13, a pressure distribution of occupant 13, humidity 100 around occupant 13, the expression 96 of occupant 13, fidget level 112 of occupant 13, and the head tilt 106 of occupant 13. In another example, occupant comfort is based on the temperature of occupant 13, humidity 100 around occupant 13, the expression 96 of occupant 13, and the head tilt 106 of occupant 13.

In one scenario, occupant support system 10 detects that occupant 13 has not been moving enough for optimal long-term comfort. Occupant support system 10 suggests comfort rejuvenation, which may include a rigorous massage and activation of ventilation based on sensor measurements. In another scenario, occupant support system 10 prepares occupant 13 for physical activity by giving a stretching massage. Occupant support system 10 provides certain colors and patterns of lighting to stimulate the body for upcoming activity (for example, blue light for stimulating serotonin production).

Each occupant health data type is rated as normal, high, or low in some embodiments. If one or more of the occupant health data used to determine an occupant state is not normal, control system 16 determines one or more vehicle system 78 to recommend to occupant 13 in order to change the occupant health data toward normal. Occupant health data and occupant state data is continually monitored and recommendations are provided until occupant health data and occupant state data are normal. Occupant medical history and conditions are taken into account in determining normal occupant health data and occupant state data.

Figure 17:
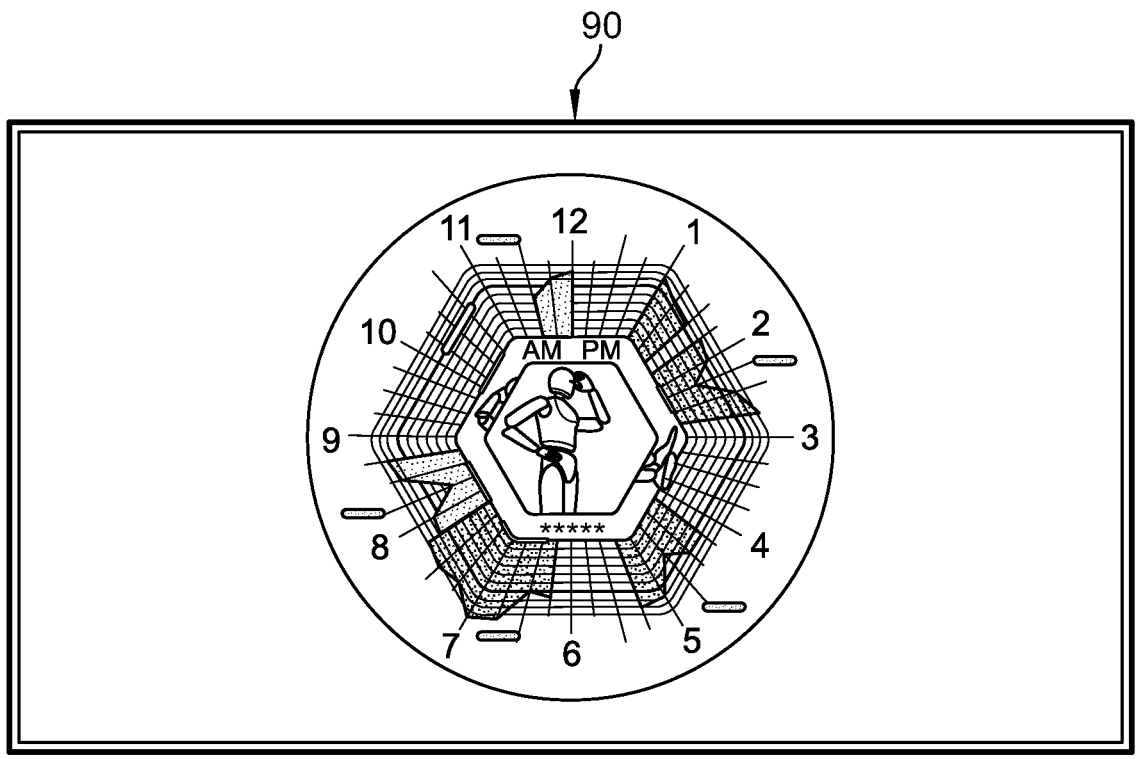
FIG. 17 is a diagrammatic view of the display included in the occupant support system showing graphical occupant health data for a 12 hour time period.

Control system 16 is configured to generate instructions to display occupant health data and/or occupant state data in a graphical representation as shown in FIG. 17. The occupant health data and/or occupant state data is graphed over a 12-hour period in the illustrative embodiment.

Occupant support system 10 is configured to cooperate with vehicle 11 and/or vehicle systems 78 to move vehicle 11 between a manual operation mode in which occupant 13 drives vehicle 11 and an autonomous operation mode in which vehicle 11 drives itself. A method 200 of moving vehicle 11 between manual operation mode and autonomous (self-driving) operation mode is shown in FIG. 18.

Method 200 includes a number of stages as suggested in FIGS. 18-22. Method 200 includes stage 202 in which occupant support system 10 indicates to the driver that autonomous driving is available. In a stage 204, autonomous driving is engaged in response to occupant input as suggested in FIG. 19. Occupant input includes clicking a button, gazing at indicia on a screen for a predetermined time, vocally responding, etc. In a stage 206, occupant support indicates that autonomous driving is engaged. As one example, display 90 shows an overhead view of vehicle 11 and its surroundings to indicate to occupant 13 that vehicle 11 is scanning and is aware of its environment during autonomous operation mode as suggested in FIG. 19. In a stage 208, occupant support system 10 monitors occupant 13 and generates wellness recommendations as discussed in detail above.

Figure 18:
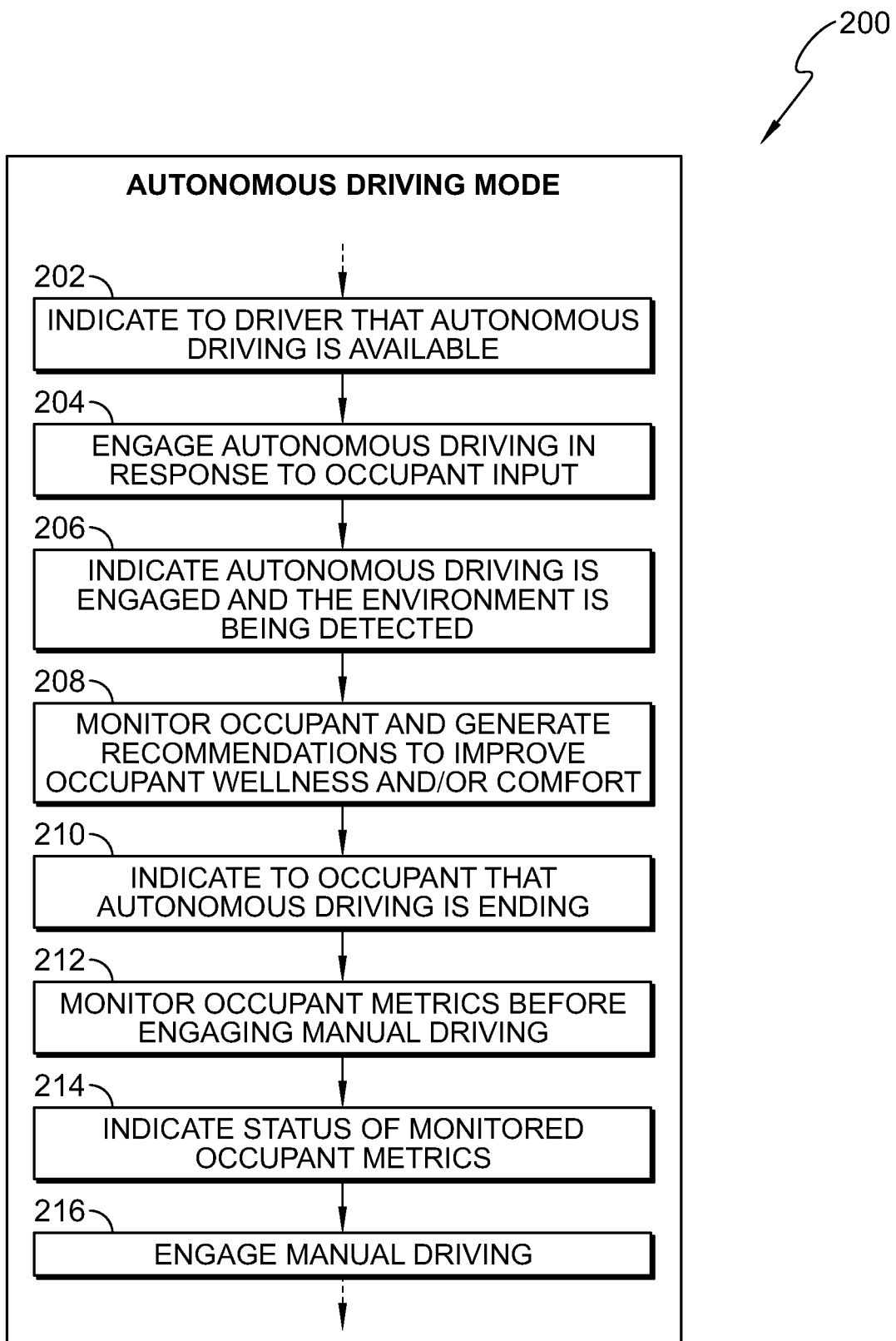
FIG. 18 is a flow chart of a method of moving the vehicle between a manual operation mode and an autonomous (self-driving) operation mode, the method including indicating to the driver that autonomous driving is available, engaging autonomous driving in response to occupant input, indicating that autonomous driving is engaged, monitoring the occupant and generating wellness recommendations, indicating that autonomous driving is ending, monitoring occupant metrics, indicating status of the occupant's metrics, and engaging manual driving.

In a stage 210, occupant support system 10 indicates that autonomous operation mode is ending as suggested in FIG. 18. In a stage 212, occupant support system 10 monitors occupant 13 metrics before moving from autonomous operation mode to manual operation mode. The status of the occupant's metrics is communicated to occupant 13 in a stage 214. Vehicle 11 engages manual operation mode in a stage 216 if occupant's metrics meet predetermined criteria as suggested in FIG. 18.

Figure 19:
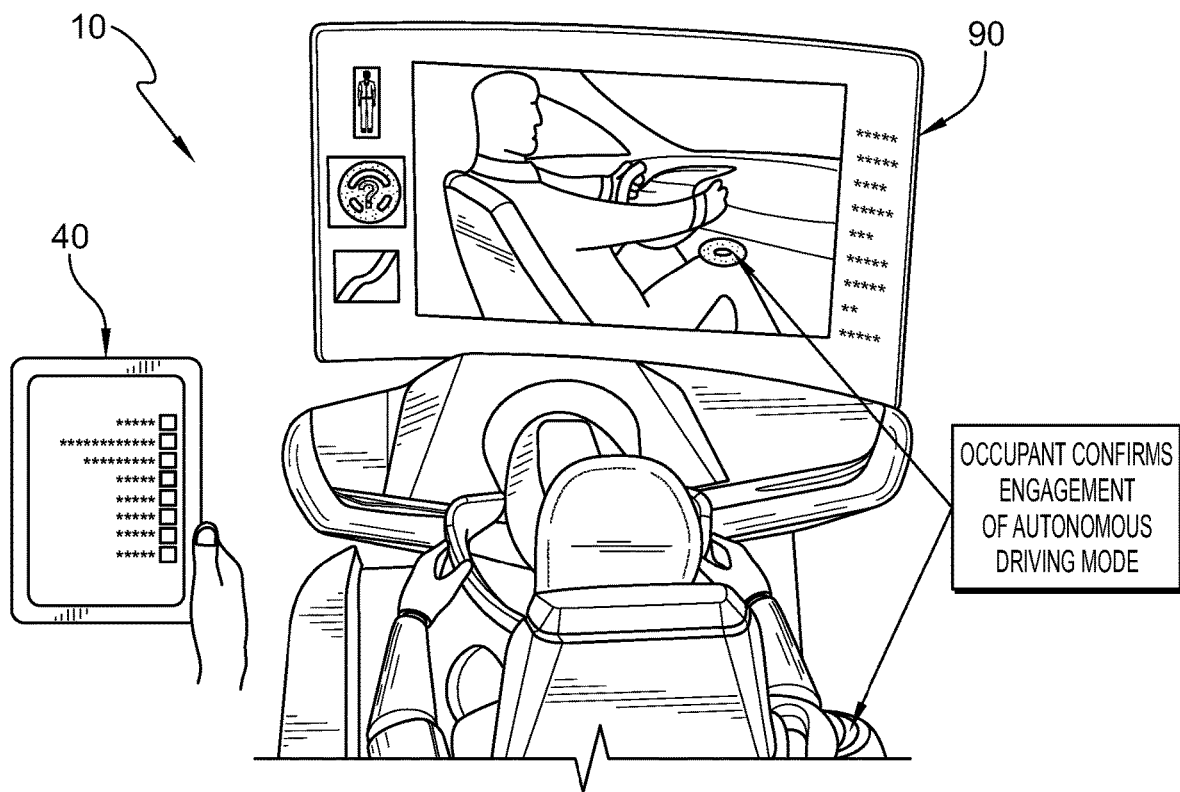
FIG. 19 is a perspective and diagrammatic view of an occupant supported in the occupant support system of FIG. 1 suggesting that the vehicle is engaging autonomous operation mode in response to the occupant's input.
Figure 20:
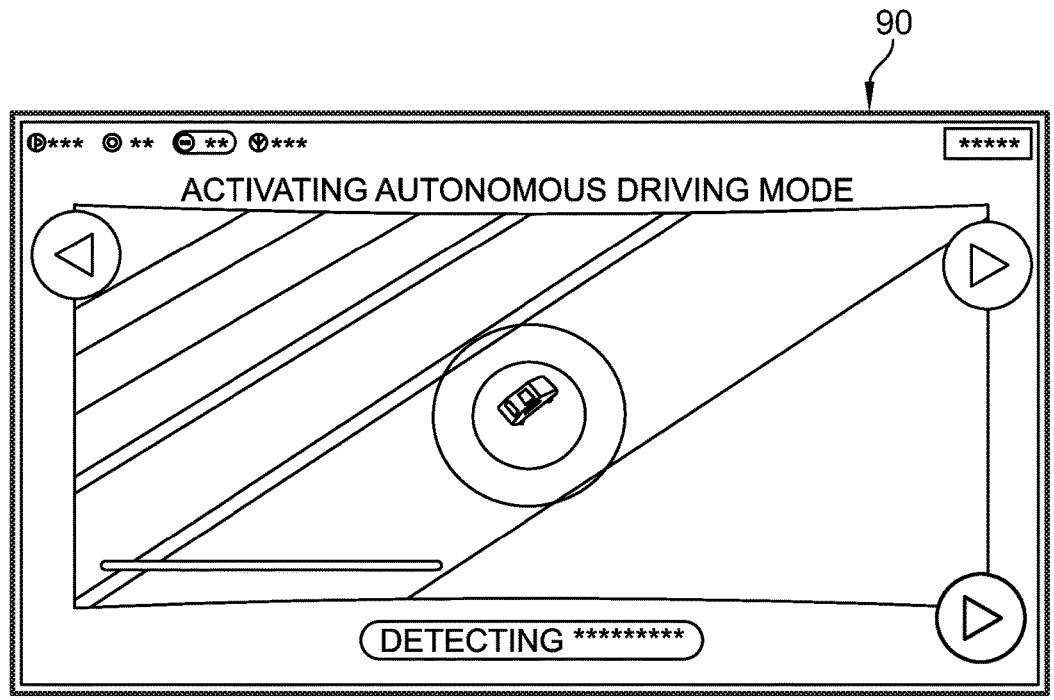
FIG. 20 is a diagrammatic view of the display included in the occupant support system showing an overhead view of the vehicle and its surroundings to indicate to the occupant that the vehicle is scanning and aware of its environment during autonomous operation of the vehicle.

Occupant 13 begins to switch from manual control of vehicle 11 to autonomous operation mode as suggested in FIG. 19. Occupant 13 affirms actions with a press of a button in the illustrative embodiment. The button may be replaced with an audible confirmation or otherwise in other embodiments. Display 90 provides a message to indicate that the occupant should "prepare to enter autonomous driving mode" and a camera angle pans backward to show the back of the occupant's head. This allows the occupant support system 10 and methods to pick out specific vehicles in the occupant vehicle's vicinity and may also indicate mirror views, giving occupant 13 confidence that the systems are aware of vehicle situational and environmental information. A specified color of light (i.e. green) on the steering column or other location indicates that occupant 13 is now clear to release the steering wheel to shift vehicle 11 into autonomous operation (self-driving) mode In stage 208, occupant 13 may perform some other activity unrelated to controlling vehicle 11. Relevant sensor data, in combination with software using proprietary algorithms, may conclude that one or more occupants are engaging in certain activities, such as reading or having a conversation with one another. Occupant support system 10 and methods provides recommendations based on the action of one or more occupants. One recommendation that the occupant may be presented with is whether or not they would like to adjust their position. As another example, if the systems conclude the occupants are engaging in light conversation, the music volume may be reduced and the lighting will be adjusted accordingly. If the systems conclude that the occupants are reading, directional light may be provided to each of the occupants and the music may be turned off.

Moreover, sensor data streams may display various indicators of what the occupant wellness systems and methods are detecting, including but not limited to, reading, conversing, adjusting position, interacting with electronic devices or other occupants, and sleeping. Occupant support system 10 and methods may provide one or more suggestions to combat the onset of motion sickness to the one or more occupants of the vehicle. The occupant(s) may affirm any request for action from the system with a press of a button. In illustrative embodiments, user activities to be learned and tracked by the systems and methods include, but are not limited to, reading, sleeping, writing, talking, looking out a window, manually-controlled driving, and autonomous-mode driving.

Figure 21:
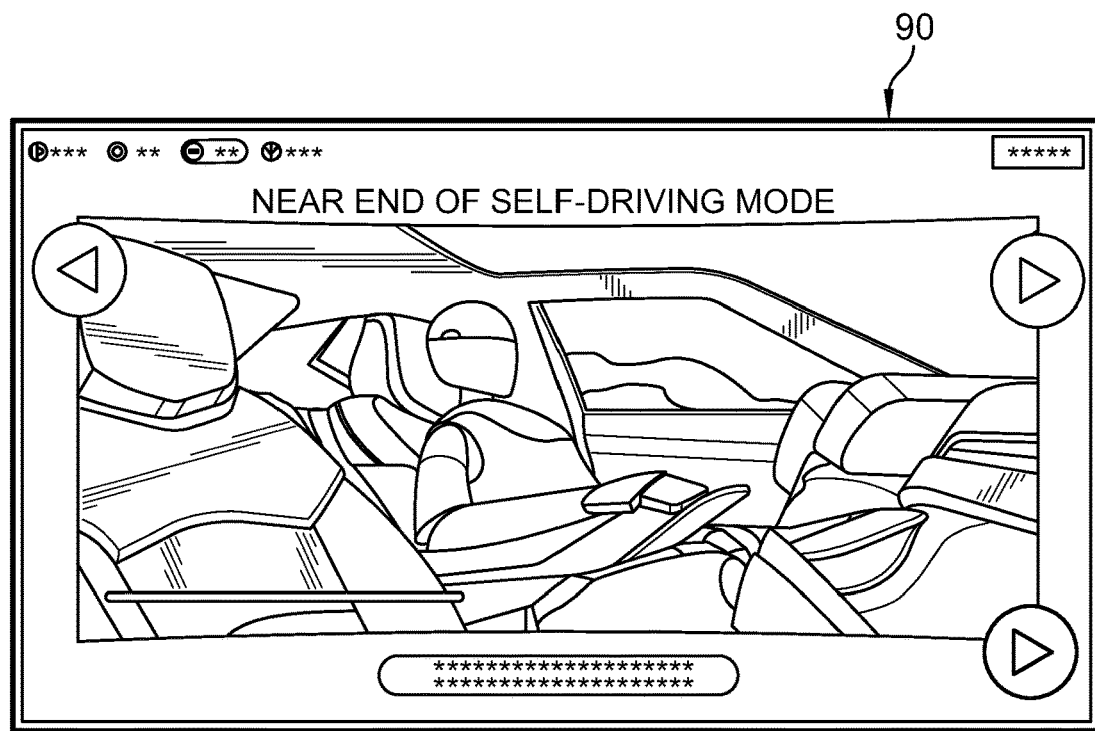
FIG. 21 is a diagrammatic view of the display included in the occupant support system showing that autonomous operation mode is ending and suggesting that the posture and position of the occupant is being monitored before the vehicles moves into the manual operation mode.
Figure 22:
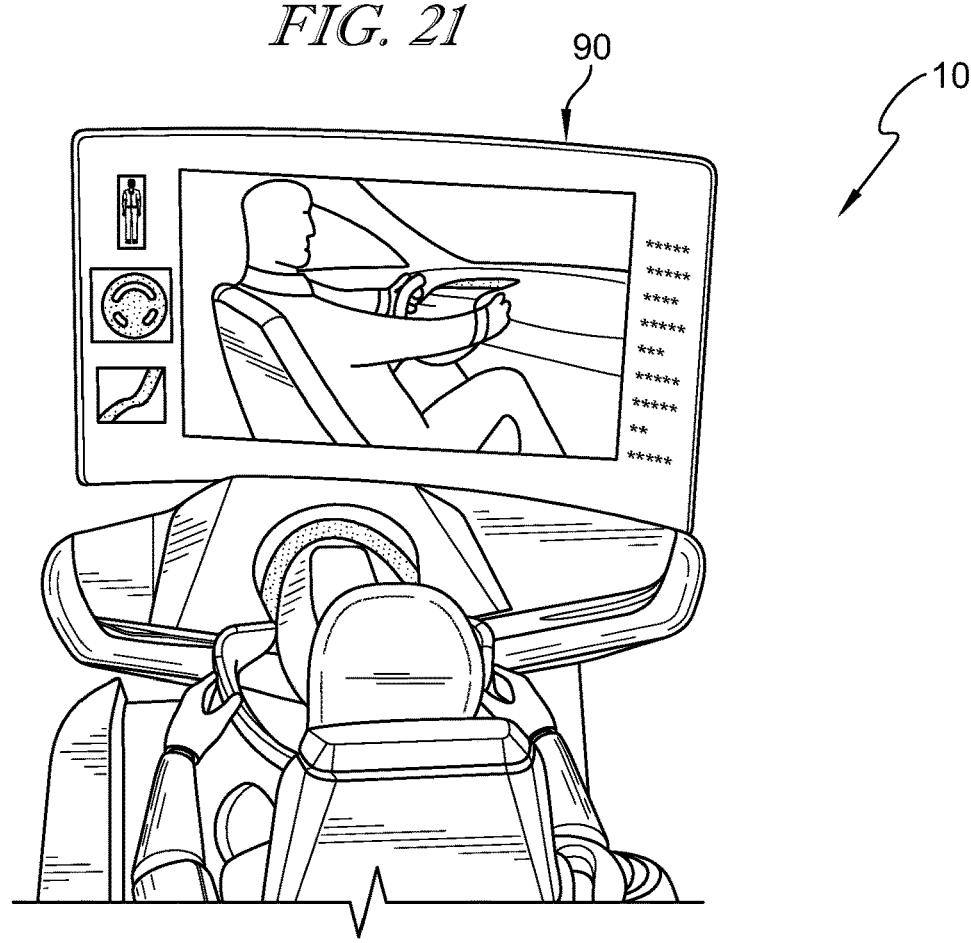
FIG. 22 is a perspective view of the occupant support system of FIG. 19 showing that the display suggests that the occupant should place their hands on the steering wheel and that hand position of the occupant is being monitored before the vehicle moves into the manual operation mode.
Figure 23:
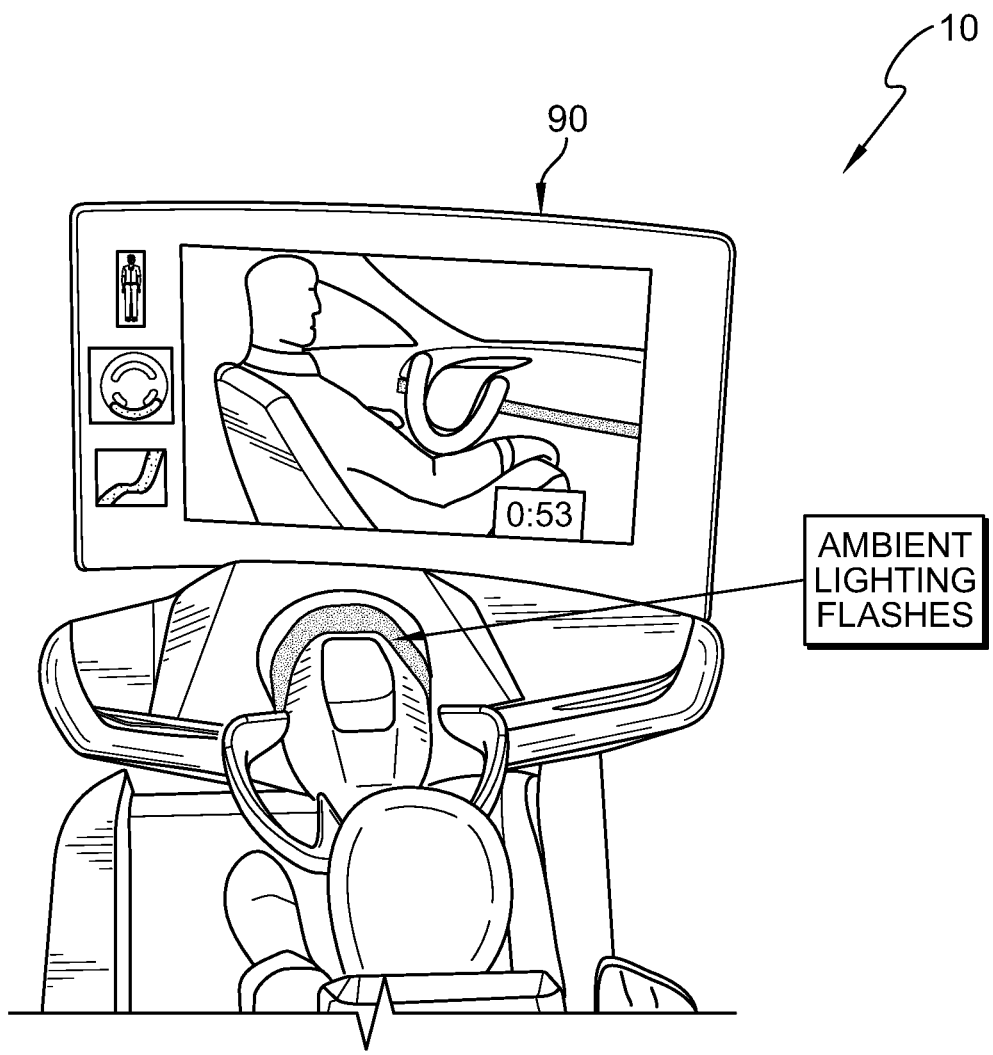
FIG. 23 is a view similar to FIG. 22 showing that the gaze of the occupant is being monitored before the vehicle moves into the manual operation mode.

During stage 212, occupant support system 10 monitors occupant body position, occupant hand position, and occupant gaze as suggested in FIGS. 21-23. If occupant body position is in a predetermined arrangement, occupant support system 10 determines that occupant body position is ready for manual operation as suggested in FIG. 21. As a result, an indication such as, for example, a light on the steering column may change (i.e. from red to green). If occupant body position is not in a predetermined arrangement, occupant support system 10 recommends changing the arrangement of seat 12 or automatically changes the arrangement of seat 12 to a predetermined arrangement.

Occupant hand position is monitored by occupant support system 10 as suggested in FIG. 22. If occupant hand position is in a predetermined arrangement, occupant support system 10 determines that occupant hand position is ready for manual operation. As a result, an indication such as, for example, a light on the steering column may change (i.e. from red to green). If occupant hand position is not in a predetermined arrangement, occupant support system 10 recommends changing the arrangement of occupant's hands.

Eye glance direction and other factors (eye tracking, face tracking, or both) shows occupant 13 is focusing in on a different field of view as suggested in FIG. 23. Mirrors may flash on-screen to evaluate the occupant's 13 awareness based upon time to focus. One or more timers may indicate elapsed time since the reengagement sequence began. Occupant looks forward at a horizon for two seconds (or other predetermined amount of time), and as a result, the ambient lighting display or a steering column light turns green to indicate that occupant 13 is ready to assume manual driving.

In some embodiments, vehicle 11 audibly announces that occupant 13 is ready to drive.

The following numbered clauses include embodiments that are contemplate and non-limiting:

Clause 1: An occupant support system for use in a vehicle, the occupant support comprising a sensor system configured to obtain occupant-body signals associated with physiological characteristics of an occupant of the occupant support system and behavioral signals associated with behavioral characteristics of the occupant.

Clause 2. The occupant support system of clause 1, any other clause, or any combination of clauses, further comprising a control system configured to receive the occupant-body signals and the behavioral signals, determine occupant health data indicative of physiological characteristics and behavioral characteristics of the occupant based on the occupant-body signals and the behavioral signals, determine occupant state data indicative of a state of the occupant based on the occupant health data, identify a first vehicle system configured to change at least one physiological characteristic or behavioral characteristic of the occupant based on at least one of the occupant health data and the occupant state data, and activate a second vehicle system based on at least one of the occupant health data, the occupant state data, and input from the occupant.

Clause 3. The occupant support system of clause 2, any other clause, or any combination of clauses, wherein the first vehicle system and the second vehicle system are the same vehicle system.

Clause 4. The occupant support system of clause 2, any other clause, or any combination of clauses, wherein the control system is further configured to identify the occupant based on at least one of input from the occupant and the occupant health data and to associate the occupant health data and the occupant state data with a unique occupant data profile for the identified occupant.

Clause 5. The occupant support system of clause 4, any other clause, or any combination of clauses, wherein the control system is further configured to associate activation of the second vehicle system with the occupant health data and the occupant state data in the unique occupant data profile.

Clause 6. The occupant support system of clause 5, any other clause, or any combination of clauses, wherein the control system is further configured to receive supplemental occupant-body signals and supplemental behavioral signals after activating the first of the plurality of vehicle systems, determine supplemental occupant health data based on the supplemental occupant-body signals and the supplemental behavioral signals, determine supplemental occupant state data based on the supplemental occupant health data, identify a third vehicle system configured to change at least one physiological characteristic or behavioral characteristic of the occupant based on at least one of the supplemental occupant health data, the supplemental occupant state data, and the unique occupant data profile, and activate a fourth vehicle system based on at least one of the supplemental occupant health data, the supplemental occupant state data, the unique occupant data profile, and input from the occupant.

Clause 7. The occupant support system of clause 6, any other clause, or any combination of clauses, wherein the control system is further configured to associate activation of the fourth vehicle system with the supplemental occupant health data and the supplemental occupant state data in the unique occupant data profile.

Clause 8. The occupant support system of clause 4, any other clause, or any combination of clauses, wherein the control system is further configured to receive supplemental occupant-body signals and supplemental behavioral signals after activating the second vehicle system, determine supplemental occupant health data based on the supplemental occupant-body signals and the supplemental behavioral signals, compare the occupant health data and the supplemental occupant health data, and associate changes to the occupant health data in the unique occupant data profile.

Clause 9. The occupant support system of clause 3, any other clause, or any combination of clauses, wherein the control system is further configured to receive secondary health data unique to the occupant from at least one of an input and an accessory device, associate the secondary data with the unique occupant data profile, determine a health score of the occupant based on the occupant health data, the unique occupant data profile, and predetermined criteria, and generate instructions to display the health score to the occupant.

Clause 10. The occupant support system of clause 3, any other clause, or any combination of clauses, wherein the control system is further configured to receive schedule data indicative of scheduled events of the occupant from at least one of an input and an accessory device and to prompt the occupant to perform an activity based on the schedule data.

Clause 11. The occupant support system of clause 2, any other clause, or any combination of clauses, wherein the plurality of vehicle systems includes a sound system.

Clause 12. The occupant support system of clause 2, any other clause, or any combination of clauses, wherein the plurality of vehicle systems includes a lighting system.

Clause 13. The occupant support system of clause 2, any other clause, or any combination of clauses, wherein the plurality of vehicle systems includes a ventilation system.

Clause 14. The occupant support system of clause 2, any other clause, or any combination of clauses, wherein the plurality of vehicle systems includes a seat including an adjustable seat bottom and an adjustable seat back.

Clause 15. The occupant support system of clause 2, any other clause, or any combination of clauses, wherein the plurality of vehicle systems includes a temperature system included in the seat.

Clause 16. The occupant support system of clause 2, any other clause, or any combination of clauses, wherein the plurality of vehicle systems includes a massage system.

Clause 17. The occupant support system of clause 2, any other clause, or any combination of clauses, wherein the sensor system includes an optical camera Clause 18. The occupant support system of clause 2, any other clause, or any combination of clauses, wherein the sensor system includes a piezoelectric sensor.

Clause 19. The occupant support system of clause 2, any other clause, or any combination of clauses, wherein the sensor system includes a woven electrode.

Clause 20. The occupant support system of clause 2, any other clause, or any combination of clauses, wherein the sensor system includes a capacitive sensor.

Clause 21. The occupant support system of clause 2, any other clause, or any combination of clauses, wherein the sensor system includes a load cell.

Clause 22. The occupant support system of clause 2, any other clause, or any combination of clauses, wherein the sensor system includes a humidity sensor.

Clause 23. The occupant support system of clause 2, any other clause, or any combination of clauses, wherein the sensor system includes a thermistor.

Clause 24. The occupant support system of clause 2, any other clause, or any combination of clauses, wherein the occupant state data is indicative of a vigilance of the occupant and based on occupant health data that includes information indicative of a respiration rate of the occupant determined from signals received from a piezoelectric sensor and an electrode included in the sensor system, a posture of the occupant determined from signals received from a load cell and an optical camera included in the sensor system, an eye gaze of the occupant determined from signals received from the optical camera, and a head tilt of the occupant determined from signals received from the optical camera.

Clause 25. The occupant support system of clause 2, any other clause, or any combination of clauses, wherein the occupant state data is indicative of a motion sickness of the occupant and based on occupant health data that includes information indicative of a humidity around the occupant determined from signals received from a humidity sensor included in the sensor system, an eye closure of the occupant determined from signals received from an optical camera included in the sensor system, an eye blink rate of the occupant determined from signals received from the optical camera, a yawn rate of the occupant determined from signals received from the optical camera, and a breathing rate of the occupant determined from signals received from a piezoelectric sensor and an electrode included in the sensor system.

Clause 26. The occupant support system of clause 2, any other clause, or any combination of clauses, wherein the occupant state data is indicative of a stress of the occupant and based on occupant health data that includes information indicative of a humidity around the occupant determined from signals received from a humidity sensor included in the sensor system, a facial expression of the occupant determined from signals received from an optical camera included in the sensor system, a heart rate of the occupant determined from signals received from a piezoelectric sensor and an electrode included in the sensor system, and a fidget level of the occupant determined from signals received from the optical camera, a capacitive sensor, and a load cell included in the sensor system.

Clause 27. The occupant support system of clause 2, any other clause, or any combination of clauses, wherein the occupant state data is indicative of a drowsiness of the occupant and based on occupant health data that includes information indicative of an eye closure level of the occupant, an eye blink rate of the occupant, a yawn rate of the occupant, and a head tilt of the occupant, each determined from signals received from an optical camera included in the sensor system.

Clause 28. The occupant support system of clause 2, any other clause, or any combination of clauses, wherein occupant state data is indicative of a comfort of the occupant and based on occupant health data that includes information indicative of a humidity around the occupant determined from signals received from a humidity sensor included in the sensor system, a facial expression of the occupant determined from signals received from an optical camera included in the sensor system, a fidget level of the occupant determined from signals received from the optical camera, a capacitive sensor, and a load cell included in the sensor system, and a head tilt of the occupant determined from signals received from the optical camera.

Clause 29. A method of controlling a vehicle, the method comprising
indicating to a driver of a vehicle that an autonomous driving mode of the vehicle is available,
engaging autonomous driving mode of the vehicle in response to receiving an affirmative input from the driver,
indicating to the driver that autonomous driving is engaged,
monitoring the physiological and behavioral characteristics of the driver,
determining occupant condition improvement instructions based on the monitored physiological and behavioral characteristics of the driver, and
activating an output based on the occupant condition improvement instructions.

Clause 30. The method of clause 29, any other clause, or any combination of clauses, further comprising indicating to the driver that a manual driving mode of the vehicle is available and initiating an autonomous-driving mode to manual-driving mode transfer process.

Clause 31. The occupant support system of clause 30, any other clause, or any combination of clauses, wherein the autonomous-driving mode to manual-driving mode transfer process includes verifying a body position of the driver, verifying an eye gaze of the driver, and verifying a hand position of the driver.

The invention claimed is:

1. An occupant support system for use in a vehicle, the occupant support comprising: a sensor system configured to obtain occupant-body signals associated with physiological characteristics of an occupant of the occupant support system and behavioral signals associated with behavioral characteristics of the occupant, a plurality of vehicle systems configured to modify at least one of the physiological characteristics and the behavioral characteristics of the occupant, and a control system configured to: organize the occupant-body signals and the behavioral signals into a plurality of experience levels, receive the occupant-body signals and the behavioral signals according to a selected one of the plurality of experience levels, determine occupant health data indicative of a plurality of physiological characteristics and behavioral characteristics of the occupant based on the occupant-body signals and the behavioral signals, determine occupant state data indicative of a state of the occupant based on the occupant health data and occupant non-driving activity data, compare the occupant state data to predetermined criteria defining one or more thresholds for the occupant state data defined by the selected experience level associated with a unique occupant data profile, identify a first vehicle system of the plurality of vehicle systems based on the occupant state data and the predetermined criteria, and activate at least one of the first vehicle system and a second vehicle system of the plurality of vehicle systems based on at least one of the occupant state data and input from the occupant, wherein the first and second vehicle systems are determined for activation according to the selected experience level.

2. The occupant support system of claim 1, wherein the control system is further configured to identify the occupant based on at least one of input from the occupant and the occupant health data and to associate the occupant health data and the occupant state data with the unique occupant data profile for the identified occupant.

3. The occupant support system of claim 2, wherein the control system is further configured to associate the activation of the activated vehicle system with the occupant health data and the occupant state data in the unique occupant data profile.

4. The occupant support system of claim 3, wherein the control system is further configured to receive supplemental occupant-body signals and supplemental behavioral signals after activating the activated vehicle system, determine supplemental occupant health data based on the supplemental occupant-body signals and the supplemental behavioral signals, determine supplemental occupant state data based on the supplemental occupant health data, identify a third vehicle system based on at least one of the supplemental occupant health data, the supplemental occupant state data, and the unique occupant data profile, and activate at least one of the first vehicle system, the second vehicle system, the third vehicle system, and a fourth vehicle system based on at least one of the supplemental occupant health data, the supplemental occupant state data, the unique occupant data profile, and input from the occupant.

5. The occupant support system of claim 4, wherein the control system is further configured to associate the activation of the second activated vehicle system with the supplemental occupant health data and the supplemental occupant state data in the unique occupant data profile.

6. The occupant support system of claim 2, wherein the control system is further configured to receive supplemental occupant-body signals and supplemental behavioral signals after the activation of the activated vehicle system, determine supplemental occupant health data based on the supplemental occupant-body signals and the supplemental behavioral signals, compare the occupant health data and the supplemental occupant health data, and associate changes to the occupant health data in the unique occupant data profile.

7. The occupant support system of claim 1, wherein the control system is further configured to receive secondary health data unique to the occupant from at least one of an input and an accessory device, associate the secondary data with the unique occupant data profile, determine a health score of the occupant based on the occupant health data, the unique occupant data profile, and predetermined criteria, and generate instructions to display the health score to the occupant.

8. The occupant support system of claim 1, wherein the control system is further configured to receive schedule data indicative of scheduled events of the occupant from at least one of an input and an accessory device and to prompt the occupant to perform an activity based on the schedule data.

9. The occupant support system of claim 1, wherein the plurality of vehicle systems includes a sound system, a lighting system, a ventilation system, a seat including an adjustable seat bottom and an adjustable seat back, a temperature system included in the seat, and a massage system.

10. The occupant support system of claim 9, wherein the sensor system includes an optical camera and a piezoelectric sensor.

11. The occupant support system of claim 10, wherein the sensor system further includes an electrode, a capacitive sensor, a load cell, a humidity sensor, and a thermistor.

12. The occupant support system of claim 1, wherein the occupant state data is indicative of a vigilance of the occupant and based on occupant health data that includes information indicative of a respiration rate of the occupant determined from signals received from a piezoelectric sensor and an electrode included in the sensor system, a posture of the occupant determined from signals received from a load cell and an optical camera included in the sensor system, an eye gaze of the occupant determined from signals received from the optical camera, and a head tilt of the occupant determined from signals received from the optical camera.

13. The occupant support system of claim 1, wherein the occupant state data is indicative of a motion sickness of the occupant and based on occupant health data that includes information indicative of a humidity around the occupant determined from signals received from a humidity sensor included in the sensor system, an eye closure of the occupant determined from signals received from an optical camera included in the sensor system, an eye blink rate of the occupant determined from signals received from the optical camera, a yawn rate of the occupant determined from signals received from the optical camera, and a breathing rate of the occupant determined from signals received from a piezoelectric sensor and an electrode included in the sensor system.

14. The occupant support system of claim 1, wherein the occupant state data is indicative of a stress of the occupant and based on occupant health data that includes information indicative of a humidity around the occupant determined from signals received from a humidity sensor included in the sensor system, a facial expression of the occupant determined from signals received from an optical camera included in the sensor system, a heart rate of the occupant determined from signals received from a piezoelectric sensor and an electrode included in the sensor system, and a fidget level of the occupant determined from signals received from the optical camera, a capacitive sensor, and a load cell included in the sensor system.

15. The occupant support system of claim 1, wherein the occupant state data is indicative of a drowsiness of the occupant and based on occupant health data that includes information indicative of an eye closure level of the occupant, an eye blink rate of the occupant, a yawn rate of the occupant, and a head tilt of the occupant, each determined from signals received from an optical camera included in the sensor system.

16. The occupant support system of claim 1, wherein occupant state data is indicative of a comfort of the occupant and based on occupant health data that includes information indicative of a humidity around the occupant determined from signals received from a humidity sensor included in the sensor system, a facial expression of the occupant determined from signals received from an optical camera included in the sensor system, a fidget level of the occupant determined from signals received from the optical camera, a capacitive sensor, and a load cell included in the sensor system, and a head tilt of the occupant determined from signals received from the optical camera.

17. A method of controlling a vehicle, the method comprising: indicating to a driver of a vehicle that an autonomous driving mode of the vehicle is available, engaging autonomous driving mode of the vehicle in response to receiving an affirmative input from the driver, indicating to the driver that autonomous driving is engaged, monitoring the physiological and behavioral characteristics of the driver, determining occupant condition improvement instructions based on the monitored physiological and behavioral characteristics of the driver and driver activity unrelated to controlling the vehicle including at least one of interactions with another occupant and destination readiness, and activating an output based on the occupant condition improvement instructions.

18. The method of claim 17, further comprising indicating to the driver that a manual driving mode of the vehicle is available and initiating an autonomous-driving mode to manual-driving mode transfer process.

19. The method of claim 18, wherein the autonomous-driving mode to manual-driving mode transfer process includes verifying a body position of the driver, verifying an eye gaze of the driver, and verifying a hand position of the driver.

* * * * *